United States Patent
Hunt et al.

(10) Patent No.: US 11,538,675 B2
(45) Date of Patent: Dec. 27, 2022

(54) RAPID IDENTIFICATION AND SEQUENCE ANALYSIS OF INTACT PROTEINS IN COMPLEX MIXTURES

(71) Applicants: Donald F. Hunt, Charlottesville, VA (US); Ann M. English, Andover, MA (US); Scott A. Ugrin, Charlottesville, VA (US); Dina L. Bai, Charlottesville, VA (US); Jeffrey Shabanowitz, Charlottesville, VA (US); John Edward Philip Syka, Charlottesville, VA (US)

(72) Inventors: Donald F. Hunt, Charlottesville, VA (US); Ann M. English, Andover, MA (US); Scott A. Ugrin, Charlottesville, VA (US); Dina L. Bai, Charlottesville, VA (US); Jeffrey Shabanowitz, Charlottesville, VA (US); John Edward Philip Syka, Charlottesville, VA (US)

(73) Assignees: University of Virginia Patent Foundation, Charlottesville, VA (US); Thermo Finnigan LLC, San Jose, CA (US)

( * ) Notice: Subject to any disclaimer, the term of this patent is extended or adjusted under 35 U.S.C. 154(b) by 490 days.

(21) Appl. No.: 16/307,615

(22) PCT Filed: Jun. 5, 2017

(86) PCT No.: PCT/US2017/035953
§ 371 (c)(1),
(2) Date: Dec. 6, 2018

(87) PCT Pub. No.: WO2017/214037
PCT Pub. Date: Dec. 14, 2017

(65) Prior Publication Data
US 2020/0312643 A1    Oct. 1, 2020

Related U.S. Application Data

(60) Provisional application No. 62/346,268, filed on Jun. 6, 2016.

(51) Int. Cl.
*H01J 49/00* (2006.01)
*G01N 33/68* (2006.01)
(Continued)

(52) U.S. Cl.
CPC ...... *H01J 49/0072* (2013.01); *G01N 33/6848* (2013.01); *H01J 49/0031* (2013.01);
(Continued)

(58) Field of Classification Search
None
See application file for complete search history.

(56) References Cited

U.S. PATENT DOCUMENTS

2003/0155502 A1    8/2003  Grosshans et al.
2003/0173524 A1    9/2003  Syka
(Continued)

FOREIGN PATENT DOCUMENTS

WO    WO2003/017319    2/2003

OTHER PUBLICATIONS

Scott Ugrin, Ion-ion Chemistry and Parallel Ion Parking for Advances in Mass Spectometric Analysis of Intact Proteins, University of Virginia, May 1, 2017, pp. 1-146; XP055651001.
(Continued)

*Primary Examiner* — Xiaoyun R Xu
(74) *Attorney, Agent, or Firm* — Barnes & Thornburg LLP

(57) ABSTRACT

The present disclosure relates to novel and improved methods of analyzing proteins, peptides and polypeptides by mass spectrometry using ion-ion reactions. More specifi-
(Continued)

cally the disclosure relates to improved methods for implementing the m/z selective arresting of ion-ion reactions within the ion-ion reaction cell of a mass spectrometer system during a period where ion-ion reactions are performed.

3 Claims, 20 Drawing Sheets

(51) Int. Cl.
    *H01J 49/04*     (2006.01)
    *H01J 49/42*     (2006.01)

(52) U.S. Cl.
    CPC .......... *H01J 49/04* (2013.01); *H01J 49/4295* (2013.01); *G01N 2560/00* (2013.01)

(56) References Cited

U.S. PATENT DOCUMENTS

| | | |
|---|---|---|
| 2005/0199804 A1 | 9/2005 | Hunt et al. |
| 2007/0164208 A1 | 7/2007 | Quarmby et al. |
| 2010/0084548 A1 | 4/2010 | Mcluckey et al. |

OTHER PUBLICATIONS

PCT Search Report and Written Opinion prepared for PCT/US2017/035953, completed Jul. 28, 2017.

Chrisman, Paul A., Sharon J. Pitteri, and Scott A. McLuckey. "Parallel ion parking: improving conversion of parents to first-generation products in electron transfer dissociation." *Analytical chemistry* 77.10 (2005): 3411-3414.

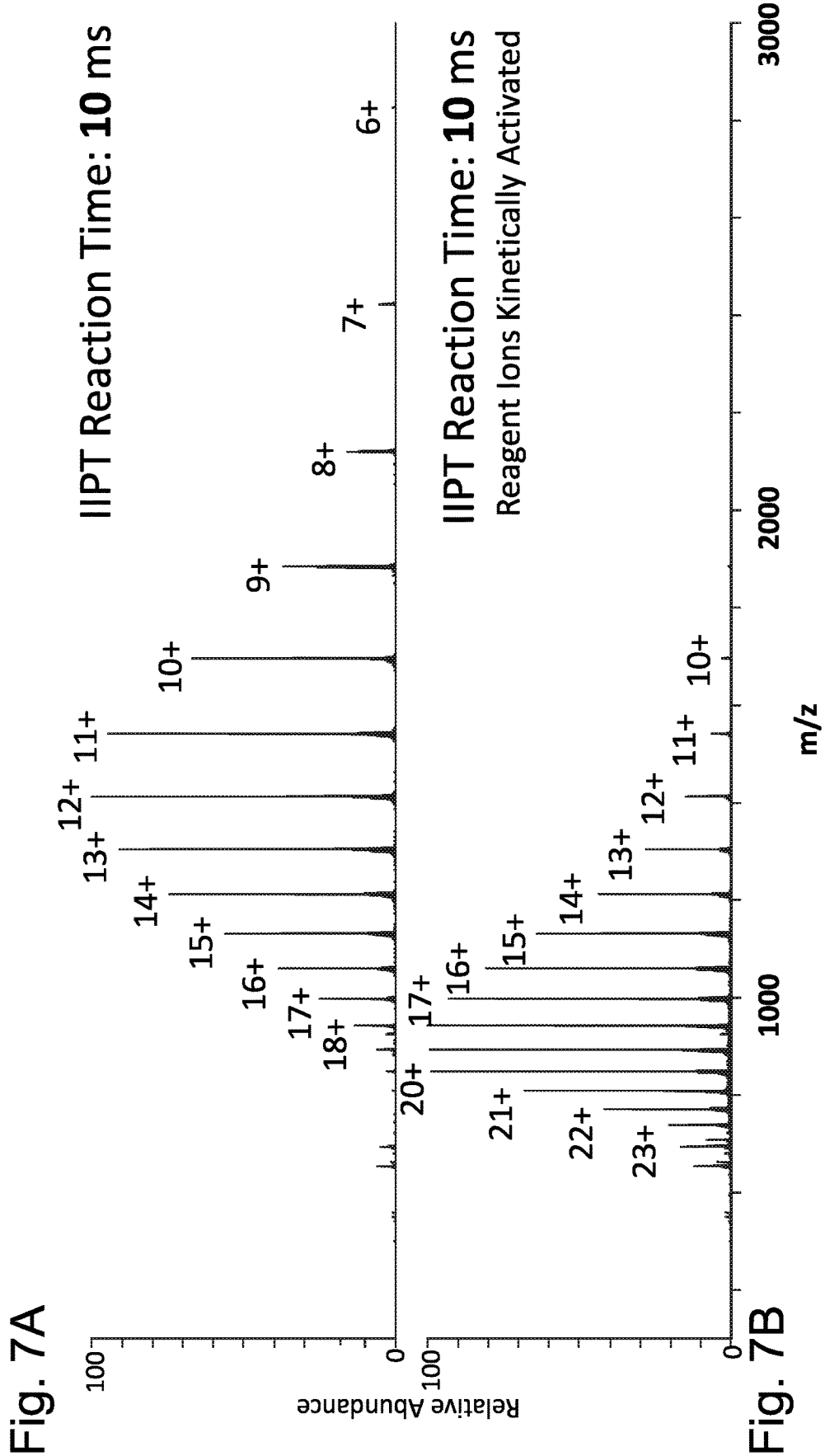
Precursor Ion: Apomyoglobin $[M+26H]^{26+}$
Fig. 7A — IIPT Reaction Time: 10 ms
Fig. 7B — IIPT Reaction Time: 10 ms, Reagent Ions Kinetically Activated

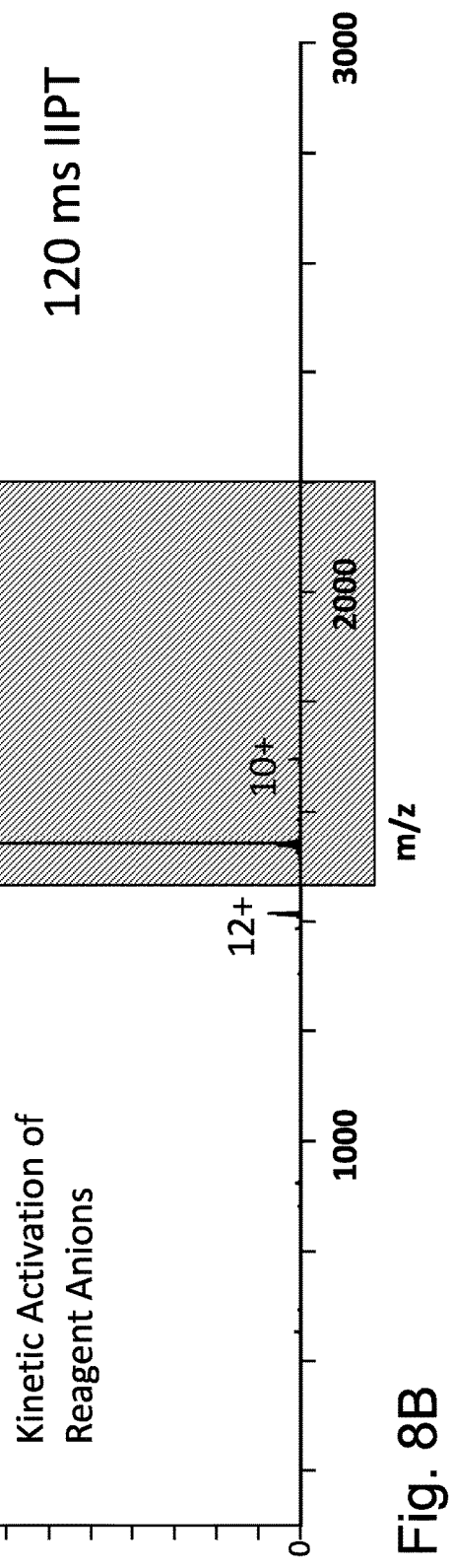

RAPID IDENTIFICATION AND SEQUENCE ANALYSIS OF INTACT PROTEINS IN COMPLEX MIXTURES

CROSS REFERENCE TO RELATED APPLICATIONS

This application is a national stage entry under 35 USC § 371 of PCT International Application Number PCT/US2017/035953, filed Jun. 5, 2017, which claims priority to U.S. Provisional Patent Application No. 62/346,268 filed on Jun. 6, 2016, the disclosures of both of which are hereby expressly incorporated by reference in their entirety.

GOVERNMENT RIGHTS

This invention was made with United States Government support under Grant Nos. GM 037537 and AI 033993, awarded by the National Institutes of Health. The United States Government has certain rights in the invention.

BACKGROUND

The identification and characterization of proteins and peptides has become a significant part of modern biology, and mass spectrometry has become one of the most important techniques used for the analysis of peptides and proteins. The present disclosure is directed to novel and improved methods of analyzing proteins, peptides and polypeptides by mass spectrometry using ion-ion reactions. More specifically the disclosure relates to improved methods for implementing the m/z selective arresting of ion-ion reactions which in the literature is referred to as ion parking. The novel methods described herein can be adapted and applied to any type of ion-ion reactions, including, but not limited to both ion-ion proton transfer reactions (referred to herein as IIPT reactions, but more generally referred to in the literature as PTR reactions of positive analyte ions) and electron transfer dissociation, ETD, reactions. The teachings herein should not be construed to imply that the inventive methods described herein are exclusively applicable to ion parking in the context of IIPT and ETD reactions. These methods can also be applied for the negative ion analyte precursor counterpart ion-ion reactions for IIPT and ETD, negative electron transfer (NETD) and proton transfer from reagent cations to analyte anions (there is no widely accepted acronym for the ion-ion reactions involving donation of protons to multiply negatively charged analyte ions). It is also expected that these methods can be applied to ion attachment ion-ion reactions. The disclosed methods provide significant advantage for ion parking when the analyte ions to be parked have relatively high charge states (9 or more charges) and become progressively more advantageous with increasing analyte ion charge state.

SUMMARY OF VARIOUS EMBODIMENTS

One aspect of the present disclosure is directed to novel and improved methods of analyzing proteins, peptides and polypeptides by mass spectrometry using ion-ion reactions. More specifically the disclosure relates to improved methods for implementing the m/z selective arresting of ion-ion reactions within the ion-ion reaction cell of a mass spectrometer system during a period where ion-ion reactions are performed. In accordance with one embodiment a method of analyzing proteins, peptides and polypeptides by mass spectrometry using ion-ion reactions is provided wherein a step of selectively arresting ion-ion reactions (ion parking) within the ion-ion reaction cell of a mass spectrometer system is conducted wherein both the reagent ions and the analyte product ions within one or more selected m/z ranges are excited so as to partially or fully arrest the further reaction of said product ions. In one embodiment the method for m/z selectively arresting ion-ion reactions (ion parking) within the ion-ion reaction cell of a mass spectrometer system is provided wherein the method comprises providing a reaction cell comprising a set of electrodes with one or more periodic RF confinement voltages applied to them wherein during ion-ion reactions in one or more dimensions of ion motion, ions have oscillatory motion frequencies that are primarily determined by their mass-to-charge ratios, applying one or more auxiliary voltage waveforms to one or more electrodes of the ion-ion reaction cell, during a period where ion-ion reactions are performed, such that a first set of frequency components of one or more of said auxiliary waveform voltages provides m/z selective kinetic excitation to the reagent ions, kinetically exciting analyte product ions within one or more selected m/z ranges, during said period where ion-ion reactions are performed, so as to partially or fully arrest the further reaction of said product ions within said selected m/z ranges. In one embodiment the analyte product ions within one or more selected m/z ranges are m/z selectively kinetically excited by a second set of frequency components of said one or more auxiliary voltage waveforms applied to the ion-ion reaction cell electrodes and where said first set of frequency components is different from said second set of frequency components. In one embodiment the one or more auxiliary voltage waveforms applied to one or more electrodes contain both said first set of frequency components and said second set of frequencies such that both the said reagent and said analyte product ions are m/z selectively kinetically excited in the same dimension of motion. Alternatively, in one embodiment the one or more auxiliary voltage waveforms applied to one or more electrodes contain both said first set of frequency components and said second set of frequencies such that both the said reagent ions and said analyte product ions are m/z selectively kinetically excited in the different dimensions of motion. In one embodiment the ion-ion reaction cell is one of the following types of devices: a RF 2D quadrupole ion trap having one or more segments or sections, a RF 3D quuadrupole ion trap, or a RF torriodal trap.

BRIEF DESCRIPTION OF THE DRAWINGS

FIG. 6A: The recorded time domain broadband parking waveform. FIG. 6B: Frequency spectrum of this same broadband parking waveform. This figure is from 2005 Chrisman et al.

FIGS. 7A & 7B Experimentally obtained product ion mass spectrum a 26+ charge state, [M+26H]26+, of Apomyoglobin for a 10 ms IIPT reaction time with perflouromethyldecalin (PFMD) reagent anions, m/z 512, q reagent ions=0.55, FIG. 7A: without kinetic activation of the reagent ions; FIG. 7B: with dipole waveform kinetic activation of the reagent ions.

FIGS. 8A & 8B Product ion mass spectra from IIPT ion parking experiments wherein the precursor ions species is the 26+ charge state, [M+26H]26+, of Apomyoglobin, the reagent anions are from PFMD (m/z 512 Da/unit charge) and held a Mathieu q of 0.55 during the reactions. The parking waveform contained a band of frequencies for kinetically activating and parking product ions in the m/z range indicated by the shaded region of the spectra (approximately 1500-2250 Da/unit charge) FIG. 8A: Spectrum from a parking experiment in accordance with the prior art wherein there were no frequency components in the parking waveform for reagent activation. The ion-ion reaction period was 25 ms. FIG. 8B: Spectrum from a parking experiment in accordance with one embodiment wherein there were added frequency components to the parking waveform that provided reagent activation. The ion-ion reaction period was extended to 120 ms.

DETAILED DESCRIPTION

Definitions

Figure 1:
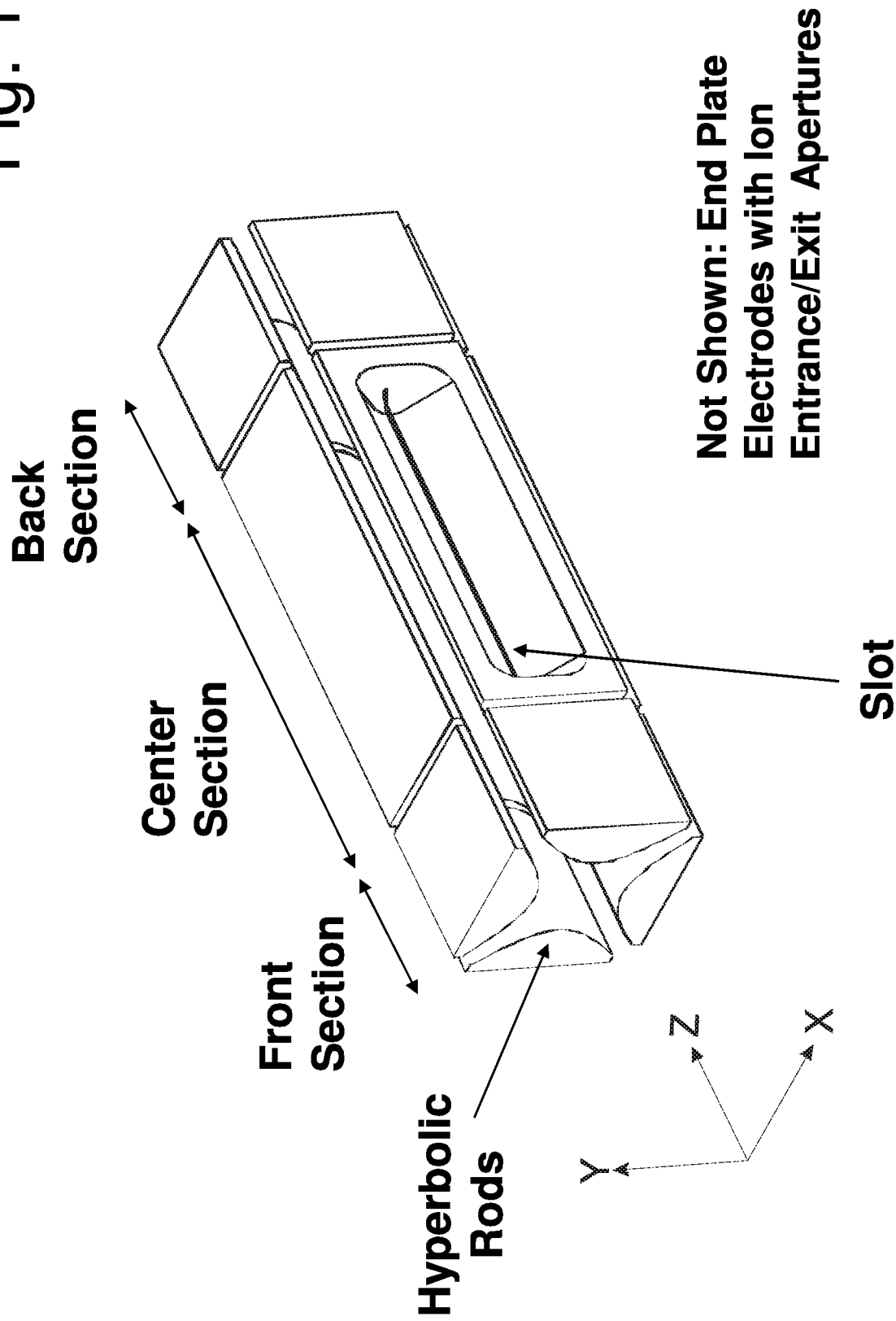
FIG. 1 A representation of a three section RF quadrupole linear ion trap electrode structure of the general type suitable for use in accordance with the present disclosure. The end plate lens electrodes with ion exit/entrance apertures are not shown.

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically $C_1$-$C_6$ alkyl groups include, but are not limited to, methyl, ethyl, n-propyl, iso-propyl, butyl, iso-butyl, sec-butyl, tert-butyl, pentyl, hexyl and the like.

As used herein the term "aryl" refers to a mono- or multi-cyclic carbocyclic ring system having one or more aromatic rings including, but not limited to, phenyl, benzyl, naphthyl, tetrahydronaphthyl, indanyl, indenyl, anthracenyl and the like. "Optionally substituted aryl" includes aryl compounds having from zero to four substituents, and "substituted aryl" includes aryl compounds having one to three substituents, wherein the substituents include hydroxyl, $C_1$-$C_4$ alkyl, halo or amino substituents.

The term "polyaromatic hydrocarbon" refers to a multi-cyclic carbocyclic ring system comprising two or more aromatic rings (selected from aryl and heteroaryl ring structures), and including but not limited to napthalene, fluorene, phenanthrene, pyrene, fluoranthene, chrysene, triphenylene, perylene, acridine; 2,2' dipyridyl; 2,2' biquinoline; 9-anthracenecarbonitrile; dibenzothiophene; 1,10'-phenanthroline; 9' anthracenecarbonitrile; and anthraquinone. "Substituted polyaromatic hydrocarbon" includes polyaromatic hydrocarbon compounds having one to three substituents, wherein the substituents include aryl, hetaryl, hydroxy, $C_1$-$C_4$ alkyl, halo, —CN, or amino substituents.

The term "heterocyclic group" refers to a mono- or multi-cyclic carbocyclic ring system containing one or more heteroatoms wherein the heteroatoms are selected from the group consisting of oxygen, sulfur, and nitrogen.

As used herein the term "heteroaryl" refers to a mono- or multi-cyclic carbocyclic ring system having one or more aromatic rings containing one or more heteroatoms (such as O, N and S) and includes, but is not limited to, furyl, thienyl, pyridyl and the like.

As used herein the term "macromolecule" refers to polymers of monomeric units or derivatives thereof, including synthetically derived polymers as well as naturally occurring polymers. Examples of macromolecules include polypeptides, polysaccharides, and nucleic acids.

The terms "polypeptide" and "protein" refer to a polymer of amino acids of at least 30 amino acids in length. This term does not specify or exclude chemical or post-expression modifications of the polypeptides of the invention, although chemical or post-expression modifications of these polypeptides may be included or excluded as specific embodiments. Modifications to polypeptides include the covalent attachment of glycosyl groups, acetyl groups, phosphate groups, lipid groups, ubiquitin groups and the like are expressly encompassed by the term polypeptide. Further, polypeptides with these modifications may be specified as individual species to be included or excluded from the present invention. The modifications of the polypeptides can occur anywhere in a polypeptide, including the peptide backbone, the amino acid side-chains and the amino or carboxyl termini. It will be appreciated that the same type of modification may be present in the same or varying degrees at several sites in a given polypeptide. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992).).

As used herein the phrase "determination of an amino acid sequence" is intended to include direct determination of the contiguous amino acid sequence, as well as a determination of a partial and/or non-contiguous sequence of a target protein, as well as the use of partial and/or non-contiguous sequences of a target protein to identify the complete sequence based on a nucleic acid or protein database search as well as identification of a protein by direct comparison of observed fragment ion masses with those expected fragments derived from known amino- and carboxy-terminal sequences of known proteins.

As used herein the term "introducing" a cation or anion, when used in the context of an ion containment device, encompasses physically inserting the ions into the containment device, as well as initiating the contact of the cations with the reagent anions. For example, introducing the ions may include the step of contacting cations and reagent anions already present in the containment device, but sequestered, by moving sequestered ions into contact within on another. Similarly, the term "removing cations/anions" will be defined as ending the contact of the cations with the reagent anions. For example, the removal of ions includes the physical removal of one of the ions from the containment device as well as the sequestering of cations and reagent anions from one another with both ions remaining within the containment device.

EMBODIMENTS

The examples in this disclosure all involve ion-ion reactions where the reagent ions are singly charged. For the examples involving ETD reactions this is because, at present, there are no known good ETD reagent anions (that is reagent anions that predominantly react by electron transfer that are multiply charged. In the advent that effective ETD reagent of higher charge state anions (and the means to generate them) are identified, the methods described herein would be still be applicable. There are a number of examples in the literature of multiply charged IIPT reagent anions (as well as reagent cations for the opposite polarity precursor experiment) produced by electrospray ionization. However the modified commercially produced instruments used to provide results described herein use discharge ion sources for production of reagent ions. Such ion sources almost exclusively generate singly charged ions as they produce them from gas phase reagent precursor compound primarily by electron capture, charge exchange and electron impact ionization processes. The ETD and IIPT reagent ions on commercial systems are presently limited to being singly charged. Again, the methods disclosed herein are expected to be applicable for m/z selectively suppressing ion-ion reactions involving either singly and multiply charged reagent ions.

The methods for effecting improved ion parking disclosed herein are for exemplary purposes described in reference their application to ion-ion reactions within ion-ion reaction cells utilizing RF quadrupole linear traps, QLTs (also referred to as RF 2D quadrupole ion traps). The ion-ion reaction cells in the instruments used for the experimental work supporting this disclosure as well as generating any of the data shown or described herein were the high pressure cells of the dual cell QLTs of modified commercial instruments. The QLTs used as the high pressure cells have three sections and a "symmetrically stretched and slotted geometry" as described in 2014 Remes et al. FIG. 1 is a depiction of the rod electrode structure shown the general attributes of these devices. There are four hyperbolically profiled rod electrodes, each divided into three electrically isolated segments. FIG. 1 does not show the insulators and other mounting means that hold the rod electrodes and rod electrode segments in fixed positions. This figure also does not show the end plate lens electrodes with ion entrance/exit aperture which are located at the front and back ends of the device. Such devices are commercially manufactured as part of commercial instruments and are well known in the art. While the herein disclosed methods are primarily described in reference to these specific types of QLT based ion-ion reaction cells, it should not be construed that these methods are limited in application to these specific types of reactions cells. Suitable ion-ion reaction cells may incorporate RF QLTs with electrode structures that have one or more of the following attributes:

Multiple longitudinal segments with segmented rod electrodes or aligned individual rod electrode sets.

Rod electrodes with interior facing sectional profiles that are in, approximation, hyperbolic, round, flat or any "non-ideal" shape. Rod electrodes may be divided in to sub electrodes of many shapes Rod electrodes may have one or multiple slots or holes in them Rod electrodes may be straight or curved and corresponding electrode structures may have straight or curved axes Additional electrodes may be incorporated into the structure that allow imposition of other potentials other than the approximate 2D quadrupole radial confinement field generated by application of the appropriate RF voltages to the rod electrodes. These additional electrodes maybe used impose additional RF axial fields to promote ion extraction or ion confinement.

As used herein in reference to QLT reaction cells, the term "non-ideal means that the rod electrode interior profiles and their relative positions from the central axis of the device do not correspond to the iso-potentials of a pure 2D quadrupole field and would include but not be limited to "stretched" geometries and non-ideal angle asymptote hyperbolic profile rod electrode geometries.

Further it should not be construed that the methods described herein are solely applicable to ion-ion reaction cells utilizing QLTs. The methods described herein may be applied to ion-ion reaction cells utilizing RF 3D quadrupole ion traps including the conventional rotationally symmetric type ones (Paul type traps). Suitable RF 3D quadrupole ion trap electrode structures for use in accordance with inventions disclosed herein include but are not limited to those with electrodes and electrode geometries as follows:

Ring and end cap electrodes with interior facing sectional profiles that are in some approximation, hyperbolic, round, flat or any "non-ideal" shape. Ring and or end cap electrodes may be divided in to sub electrodes of many shapes Ring and end cap electrodes may have one or multiple slot or holes in them Additional electrodes may be incorporated into the structure that allow imposition of other potentials other than the approximate 3D quadrupole radial confinement field generated by application of the appropriate RF voltages to the rod electrodes. These additional electrodes maybe used impose additional RF axial fields to promote ion extraction or ion confinement.

As used herein in reference to 3D Quadrupole reaction cells, the term "non-ideal means that the rod electrode interior profiles and their relative positions from the central axis and of the device do not correspond to the iso-potentials of a pure 3D quadrupole field and would include "stretched" geometries and non-ideal angle asymptote hyperbolic profile rod electrode geometries.

Various other related RF field ion confinement devices other than RF 2D and 3D quadrupole field devices may be used as ion-ion reaction cells and some of these would be would also be suitable for application of methods disclosed herein. These would include but not be limited to RF torroidal type ion traps (see U.S. Pat. No. 5,420,425).

Figure 2:
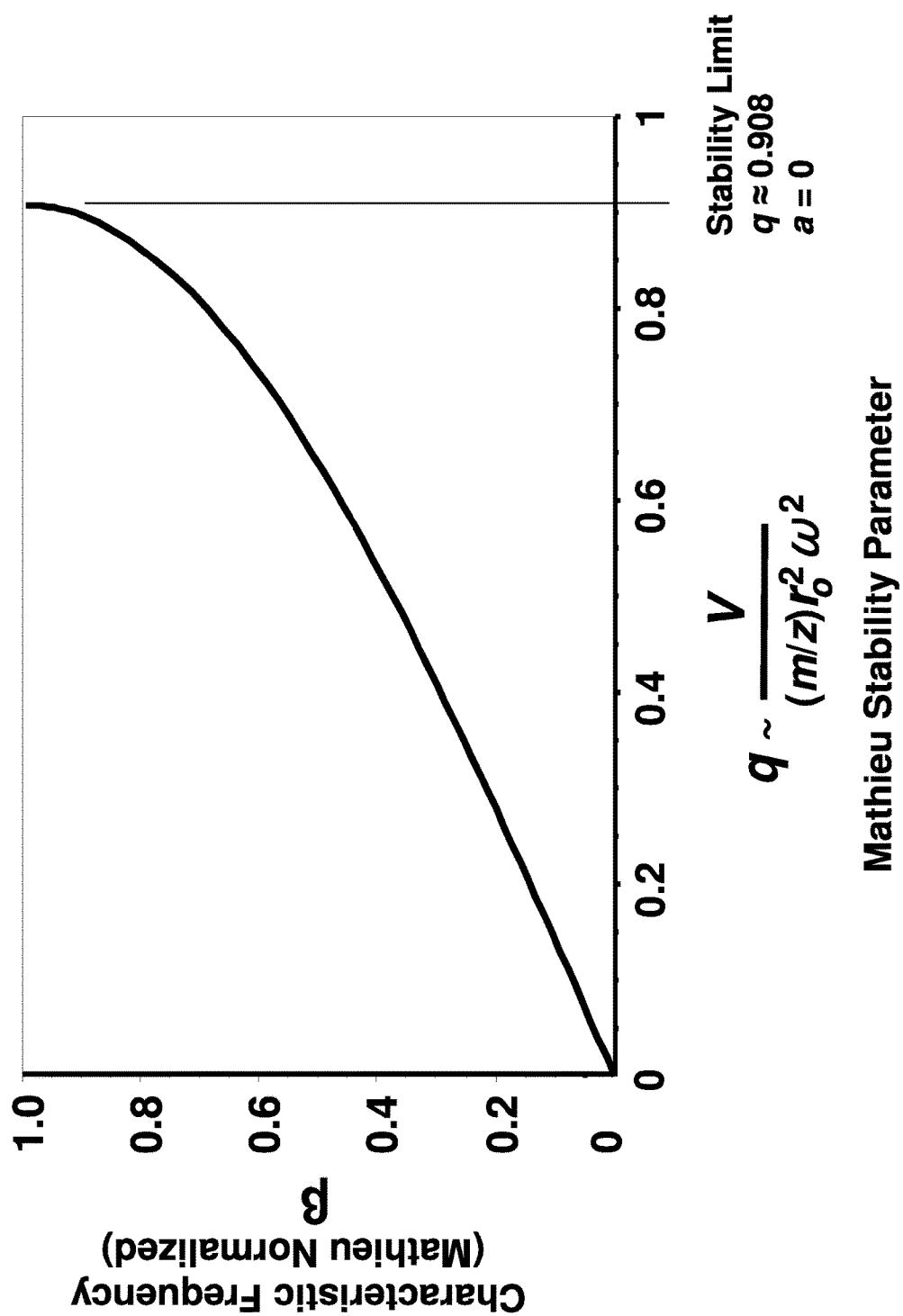
FIG. 2. A graph showing the dependence of the characteristic frequency, $\beta$, of the oscillatory solutions of the homogenous Mathieu differential equation as a function of the Mathieu stability parameter, q, for the range from q=0 to q=0.908 (the stability limit) for the case where the Mathieu stability parameter, a, is zero.

In general, the methods described herein can be applied to RF ion trapping devices that provide RF confinement fields which, in one or more dimensions, ion motion can be approximately described by Mathieu type or in the case of periodic but non-sinusoidal applied trapping RF voltages and thus trapping field, Hill type differential equations, such that for a given trapping RF field frequency and magnitude (as determined by the trapping field establishing voltages applied to the electrodes) ions have well defined ion characteristic frequencies of motion that are principally a function of m/z. Detailed expositions of the theory of ion motion in RF quadrupole field devices and the characteristics and properties of solutions homogeneous and inhomgenous Mathieu equations are available in the literature. The books 1976 Dawson and 2005 March and Todd are two such examples. Hence ion characteristic frequencies of motion in such dimensions are specific to ion m/z for a given set of trapping field imposing voltages to the device's electrodes. FIG. 2 shows the dependence of ion characteristic frequency as a function of Mathieu parameter, q, for the case where the Mathieu parameter, a, is zero. This corresponds to case where there is no DC (direct current, static) component of the quadrupole field which is generally the case when RF quadrupole trapping devices are used for ion-ion reaction cells as RF only operation gives the widest m/z range for stable trapping of ions. The Mathieu parameter q is proportional to the magnitude of the applied RF trapping field voltage, V, and inversely proportional to the ion m/z, the square of the RF angular frequency, $\omega^2$, and the characteristic dimension of the device, $r_0^2$. FIG. 2 shows the dependence of the ion characteristic frequencies in the normalized form used for solutions to the Mathieu equation on Mathieu q. Since in this normalization the angular frequency, w, of the RF field is 2, an ion's characteristic frequency will be $\beta\omega/2$. It is acceptable that there can be some weak dependence of these ion characteristic frequencies of motion on the oscillation amplitude in the particular dimension. Suitable RF trapping devices (such as those with the electrode geometries described above) will have generally some weak ion oscillation amplitude dependence in ion motion characteristic frequencies. The 2D and 3D quadrupole field ion confinement devices described above meet these requirements in 2 and 3 dimensions respectively. However, RF ion trapping devices with electrode structures that impose predominantly higher order multipole confinement fields, such as RF 2D hexapole or RF 2D octopole fields, would not satisfy these criteria in the dimensions that these fields act.

Figure 3:
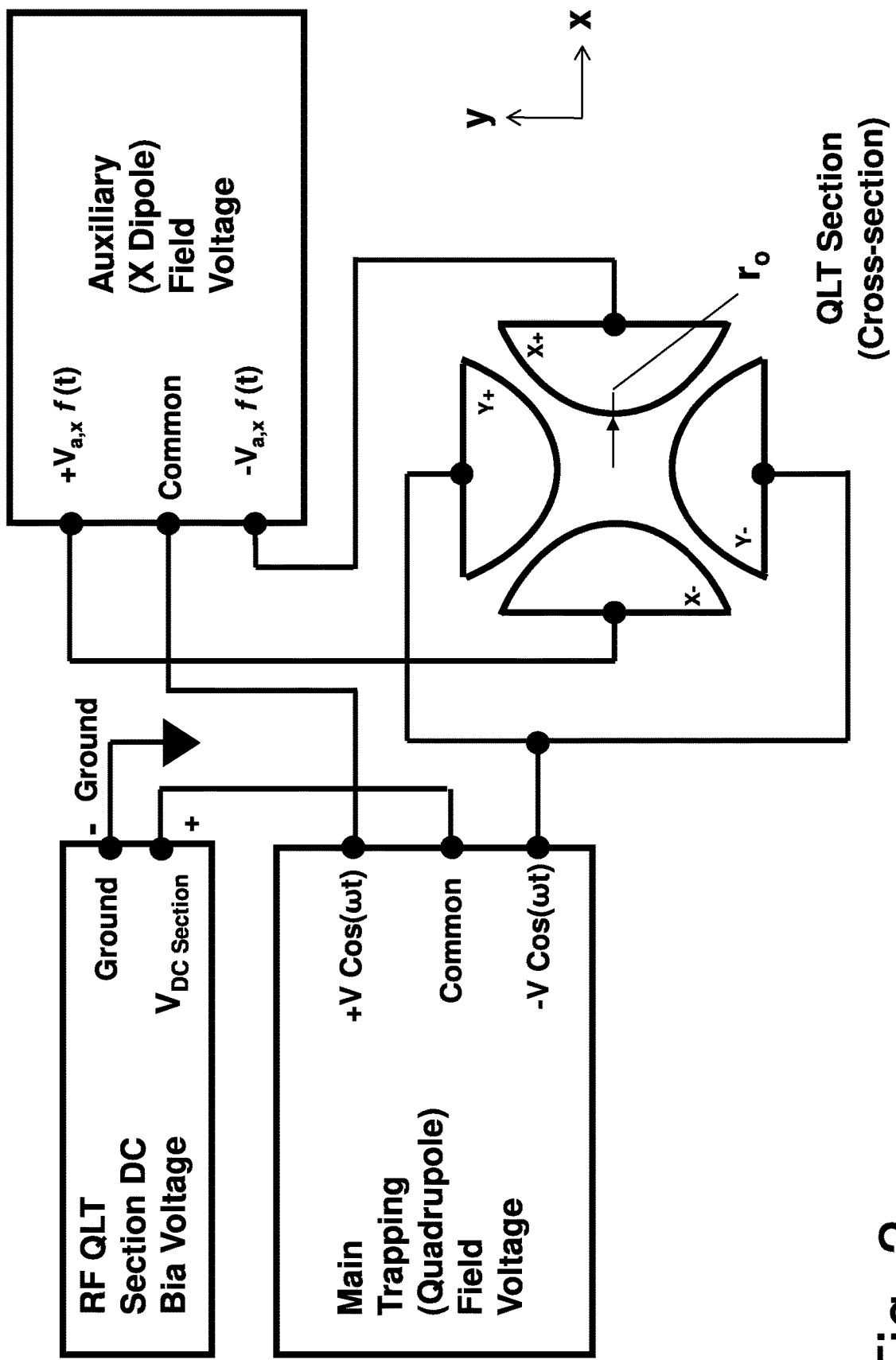
FIG. 3. A schematic representation of how the voltages are applied to the electrodes of each section of a radio frequency (RF) quadrupole linear ion trap to provide the main RF trapping field and the auxiliary (nominally dipolar) waveform fields.
Figure 4:
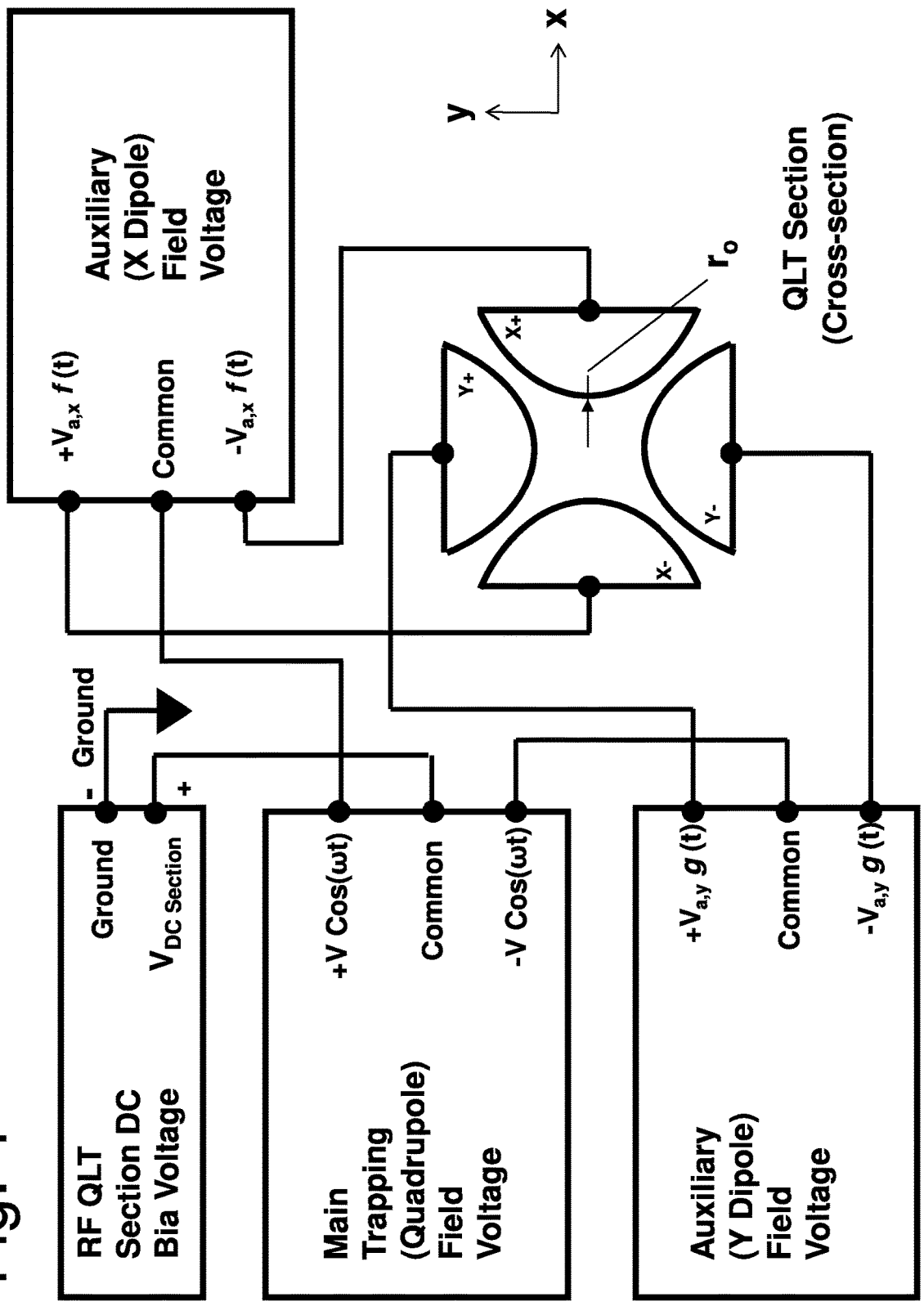
FIG. 4. A schematic representation of how the voltages are applied to the electrodes of each section of a radio frequency (RF) quadrupole linear ion trap to provide the main RF trapping field and two auxiliary (nominally dipolar) waveform fields, one acting in the x-dimension and one acting in the y-dimension.

A further general requirement for the RF ion trapping devices that are suitable for the applying the methods described herein is that there be provision for applying one or more AC auxiliary voltages to one or more of the electrodes of such RF trapping devices. These auxiliary voltages may be single frequency or may be made from the superposition of multiple frequency components. Such AC voltages are referred herein as waveform voltages. Waveform voltages may be superposed on to the trapping RF voltages applied device electrodes. Such waveform voltages may also be applied to electrodes that do not have trapping RF voltages. Application of these one or more auxiliary waveform voltages produces one or more auxiliary waveform fields that are superposed on the RF confinement fields and are used to m/z selectively kinetically excite confined ions. The amplitude, frequency and phase composition of these waveforms should be controllable so as to allow control over what ions are kinetically excited. FIG. 3 and FIG. 4 are simplified schematics indicating how trapping RF voltages, auxiliary waveform voltages and DC section bias voltages may be combined on to the QLT electrodes. During ion reactions the DC section bias voltages are usually the same (usually 0 V) during the ion-ion reactions. The RF voltages are applied differentially between opposing rods and are common to all rod segments. In FIG. 3 a single AC waveform voltage of amplitude $V_{a,x}$ and temporal variation defined by function, f(t), applied differentially between the opposing x-rod electrodes, denoted x+ and x−, to impose a nominally dipolar AC waveform field oriented and acting in the x dimension. The imposed waveform field will have lesser higher odd order (hexapole and higher order) x axis oriented multipole potential field components. FIG. 4 has all of the features of FIG. 3 but with an additional means to impose a second AC waveform voltage of amplitude $V_{a,y}$ and temporal variation defined by function, g(t), applied differentially between the opposing y-rod electrodes, denoted y+ and y−, to impose a nominally dipolar AC waveform field oriented and acting in the y dimension. This second waveform field y axis oriented imposed waveform field will also have lesser higher odd order (hexapole and higher order) y axis oriented multipole potential field components. The actual circuitry used to combine these voltages may be rather involved. There are various methods known in the art to apply such combinations of voltages. U.S. Pat. No. 6,844,547 describes one set of methods suitable for applying these potentials to QLT and related devices.

While FIGS. 3 and 4 are directed to RF 2D Quadrupole field devices, the general concept would be applicable to the RF 3D quadrupole trapping devices. The electrodes denoted as x+ and x− could be considered as the end cap electrodes and the electrodes denoted y+ and y+ could be considered together as the ring electrode. For FIG. 4 where the y+ and y− electrodes have the second AC waveform voltage applied differentially between them, these electrodes can be considered electrically isolated half sections of a ring electrode (split in the xz plane). The x− axis of the device would be the axis of symmetry for the device.

Figure 5:
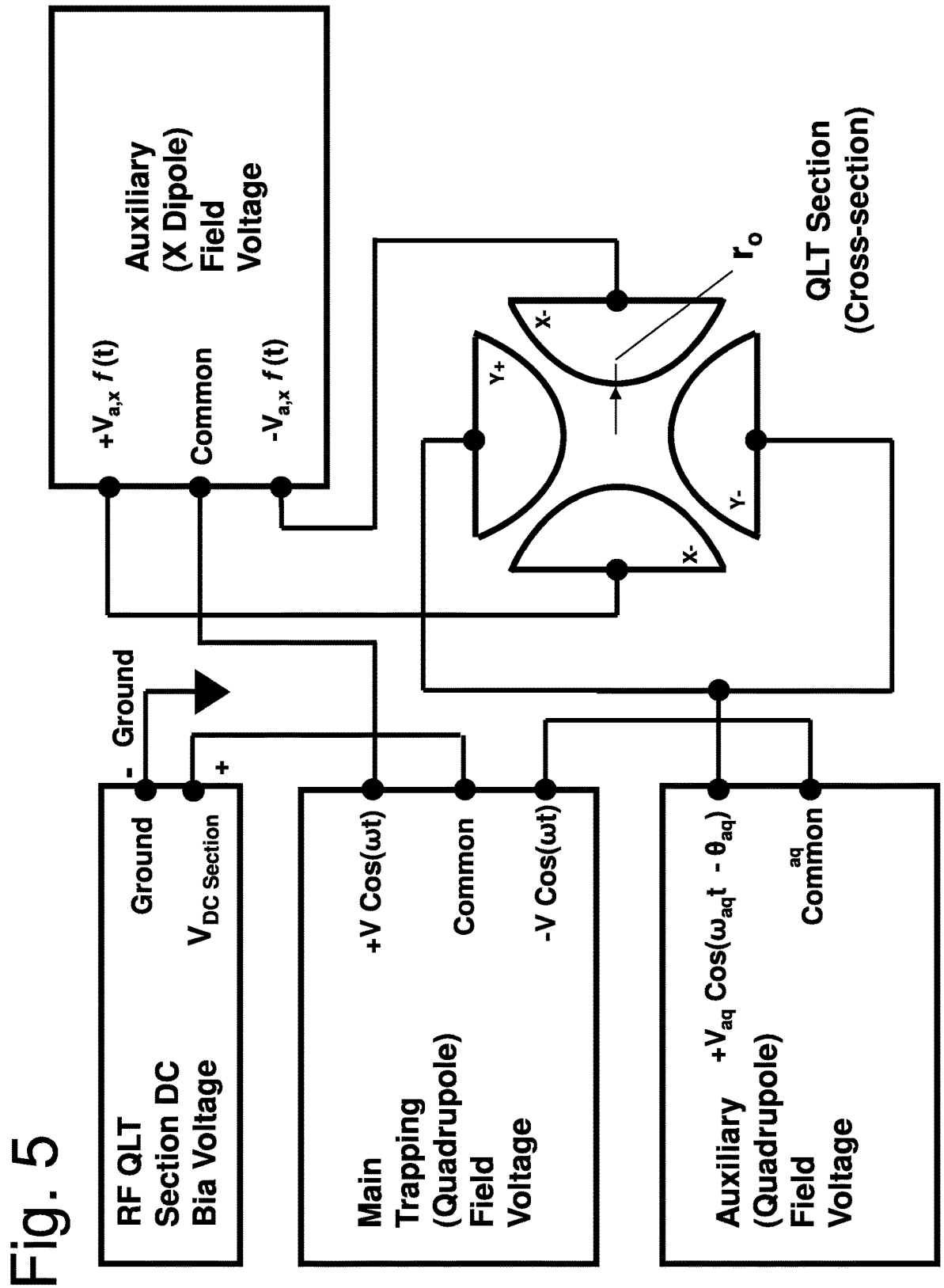
FIG. 5. A schematic representation of how the voltages are applied to the electrodes of each section of a radio frequency (RF) quadrupole linear ion trap to provide the main RF trapping field, one auxiliary (nominally dipolar) waveform field used for providing kinetic activation of analyte product ions and additionally an auxiliary nominally quadrupole waveform field for providing kinetic activation of reagent ions both the x and y dimensions via parametric resonance.

FIG. 5 has all of the same features as FIG. 3 with the addition of a voltage means to apply a second auxiliary voltage in order to establish an auxiliary AC quadrupole potential. In this particular embodiment the auxiliary voltage is sinusoidal having amplitude, $V_{aq}$, angular frequency, $\omega_{ay}$, and phase $\theta_{aq}$ and is applied to all segments of both the y+ and y− rod electrodes. Other embodiments could have the second auxiliary voltage applied differentially between the pairs of opposing rod electrodes just as the trapping field voltages are. Further, the second auxiliary voltage need not necessarily be sinusoidal (single frequency) however it is believed that it is preferred.

FIGS. 3, 4 and 5 illustrate in general how RF trapping and auxiliary voltages may be applied and superposed to produce RF quadrupolar and auxiliary dipole or auxiliary quadrupole potentials but are not intended as limiting the scope of the invention to any particular method or approach to generating these potentials inside the ion trap.

The RF QLTs used as the reaction cells for developing the improved methods for ion parking herein disclosed use Helium as a buffer/damping/collision gas. Helium is routinely used in RF ion traps which can be used as m/z analyzer or for m/z isolation and resonant collision induced dissociation (trap type CID). Hydrogen and other gases may be used but generally Helium and Hydrogen are preferred. Typical Helium pressures for such QLTs are in the range of 0.5 to 10 mTorr. For RF traps that are simply ion-ion reaction cells or serve both as ion-ion reaction cells and collision cells and are not used for m/z analysis then higher molecular weight buffer/damping/collision gases such as but not limited to Nitrogen, Argon Neon may be advantageous.

While all of the experimental work has involved effecting m/z selective arresting of ion-ion reactions where both the reagent ions and analyte ions are co-trapped in the RF field device, it is possible the methods disclosed and described herein are advantageously applicable to ion-ion reaction cells wherein only the reagent ion or the analyte ions are trapped and the oppositely charged reaction counterpart ions (analyte ions or reagent ions respectively) are passed through the ion trap. Such devices and their operation are described in Liang and McLuckey, U.S. Pat. Nos. 7,842,917 and 7,355,169.

The ion-ion reaction cells suitable for application of the methods disclosed herein may also be operated to serve as m/z selectors and m/z analyzers. The QLT analyzer of the types described in U.S. Pat. No. 5,420,425 would be examples of such devices though they would not constitute an all-inclusive list. Similarly, the RF 3D quadrupole traps in described in U.S. Pat. No. 7,456,397 would be examples though again these would not constitute an all-inclusive list. Alternatively, such suitable ion-ion reaction cells may be also operable to act as cells for performing other forms of ion dissociation such as, but not limited to, collision induced dissociation (CID) and photo-dissociation (for example 2013 Rose et al.). Other devices may be used for m/z selection and m/z analysis of precursor and product ions.

Suitable ion-ion reaction cells may be part of a mass spectrometer system that incorporates other m/z analyzers from a list including but not limited to various combinations of 2D and 3D RF ion traps, RF quadrupole m/z filters, Orbitrap™ m/z analyzers, Fourier Transform Ion Cyclotron Resonance (FT-ICR) m/z analyzers, time-of-flight (TOF) m/z analyzers. The following list of references enumerates a variety of instrument configurations which would be amenable to incorporation of ion-ion reaction cells that could be operated in accordance with the methods disclosed herein: 2005 Xia et al., 2006 Xia et al., 2013 Senko et al., 2013 Rose et al, 2013 Ledvina et al, 2008 Kaplan et al., and 2015 Hendrickson et al. This list is only exemplary and not all-inclusive.

Ion parking is the m/z selective control of the kinetics of ion-ion reactions in an ion confinement or containment device (reaction cell). The purpose is to shield certain m/z ranges of analyte product ions produced by ion-ion reactions from being subjected to further ion-ion reactions. Ion parking was first described and implemented by the McLuckey group at Purdue University in 2002 (2002 McLuckey et al, 2002 Reid et al, U.S. Pat. Nos. 7,064,317 and 7,355,169).

In this work single frequency auxiliary dipole fields were applied to m/z selectively kinetically activate (resonant activation and near-resonance/off resonance activation) to suppress the kinetics of further proton transfer charge reduction reactions for certain charge reduced product ions in RF 3D quadrupole ion traps. Since the auxiliary dipole fields (and corresponding applied voltages) used to kinetically activate the analyte product ions were single frequency (sinusoidal), the m/z range for ion parking was rather narrow. Generally, the parking m/z region with was sufficient to fully contain the isotopic m/z peak distribution of a multiply charged peptide or protein ion species of a specific charge. While these papers described ion parking methods for proton transfer reactions (IIPT/PTR) between multiply protonated polypeptides (the analyte ions) and singly charged an reagent anions, the techniques described in these papers could be used to m/z selectively arrest other types of ion-ion reactions including those involving reagent cations and analyte anions.

Also in 2002 a group from Hitachi filed two patents that describe an approach to ion parking in RF 3D quadrupole ion traps than differs significantly from the approach described by McLuckey et al. The first of these patents, U.S. Pat. No. 6,570,151, describes using an axial DC dipole field to m/z dependently control the progression of charge reduction ion-ion reactions in a RF 3D quadrupole ion trap. The DC axial dipole field was created by applying differential DC voltages to the end cap electrodes of the 3D quadrupole trap. The DC dipole field serves to axially displace the analyte ion and reagent ion clouds from the 3D RF quadruple field center in opposite directions along the device's axis (axis of rotational symmetry, z-axis). The reagent anions are presumed to be of lower m/z than any of the analyte ions (precursor as well as all successive generation product ions) are confined in the trap at a relatively high Mathieu q-value. This means that the displacement of center of the reagent ion cloud toward the end cap with the positive polarity is relatively small. The analyte ions are presumed to be of higher m/z than the reagent ions (the specification only discusses charge reduction ion-ion reactions such as IIPT/PTR) and the centers of the ion clouds for precursor and product analyte ions are displaced towards the end cap with negative polarity DC voltage. The precursor analyte ions have the highest charge states and therefore have the lowest m/z of the analyte ions since the other analyte ions are simply charge reduced versions of the precursor ions. As the analyte ions are subjected to a succession of non-dissociative charge reduction ion-ion reactions, the analyte ions include populations of ever more charge reduced product ions which have correspondingly higher m/z charges. The axial displacements of the centers of the ion clouds for each charge reduced analyte ion species is progressively greater with the m/z (lower charge state, Z) since the action of the RF field is weaker for higher m/z as they have lower Mathieu q-values and corresponding characteristic frequencies. This reduces the overlap of the ion clouds of the more charge reduced (lower charge state) analyte product ions with the reagent ion cloud. It results in progressively lower rates of reaction for analyte product ions as they undergo sequential charge reduction reactions in comparison to what would be expected based simply on the $Z^2$ dependence of the reaction rate constants. With sufficient charge reduction (and with appropriately chosen DC applied voltages to create the DC dipole field) the ion clouds of sufficiently charge reduced product analyte ions may fully (or almost fully) separate from that of the reagent ions effectively stopping any further charge reduction reactions. The m/z at which this "parking" will occur can be controlled by the choice of the magnitude of RF trapping field voltage (the trap size and frequency is presumed to be fixed) and the magnitude of the differential DC (dipole) voltage applied between the end cap electrodes.

The second of the patents, U.S. Pat. No. 6,674,067, builds on the idea of the first Hitachi patent. It teaches the use of AC dipolar fields in addition to the dipolar DC field of the first patent (U.S. Pat. No. 6,570,151 B1) to effect m/z selective reaction of analyte ions. The magnitude of the RF trapping voltage (the frequency of the trapping field is presumed to be fixed) and the DC dipole field imposing voltages are chosen so that the reagent ion cloud and the precursor analyte ions ion cloud are fully separated and thus ion-ion reactions are suppressed. Application of a single frequency or a multi-frequency dipole field which is aligned with the DC dipole field m/z selectively kinetically activates analyte ions and producing collective oscillatory motion. At one of the extremes of the collective ion motion the kinetically activated precursor ion cloud overlaps with the ion cloud of the reagent ions allowing reactions to occur. The magnitude and frequency composition of the supplemental differential AC voltage is selected to achieve this. Once an activated analyte ion undergoes a reaction the m/z of the resultant product is almost certainly different from that of the precursor ion. Unless the m/z of this product ion is also being kinetically activated by frequency components of the auxiliary AC dipole field, the damping of the Helium (or other damping/buffer/collision gas) causes the product ion oscillation to relax near thermal (or low) energy oscillations about the equilibrium displacement for product ion m/z in the combined RF quadrupole and DC dipole fields. This removes the product ion from exposure to the reagent ion cloud. As long charge state of an activated product ion m/z is not so high (it is assumed here that the reagent ions have only a single the charge—which is generally but certainly not universally the case—so that there are no charge reduced reagent product ions) that such analyte product ions will have a reaction rate with the reagent ion population that it is likely to undergo a subsequent reaction with a reagent ion before its trajectory damps such that no part of its oscillatory trajectory takes it into the reagent ion cloud, ions of that m/z will be effectively "parked". In this mode the analyte ions that are subjected to kinetic activation are the ions that are subject to ion-ion reactions and all other analyte ions are "parked". This is the exact opposite of how it is for the methods developed in the McLuckey lab. It is the first description of a "parallel ion parking method" as large ranges of ions (multiple different species) could be simultaneously "parked".

While the "ion parking" methods described in U.S. Pat. Nos. 6,570,151 and 6,674,067 were described for RF 3D quadrupole ion traps these methods, as of this present date, are readily and obviously applicable/adaptable to RF 2D quadrupole traps and related devices. The dipole fields are simply created by applying differential DC and AC voltages to opposing rod electrodes while applying RF end fields to create axial confinement of both the analyte and reagent ion populations thereby effecting co-trapping of anions and cations in the same region of the 2D quadrupole trap.

After Electron Transfer Dissociation was developed (see 2004 Syka et al, 2004 Coon et al. and U.S. Pat. No. 7,534,622), the McLuckey group adapted their approach to "ion parking" in order to inhibit the further reaction of first generation polypeptide analyte ETD product ions. In U.S. Pat. No. 7,534,622, it was suggested that the then known ion parking techniques, which before had only been described in the context of non-dissociative charge reduction reactions, could be adapted for use with ETD. However it only discussed this in general terms. The application of ion parking methods to ETD reaction was believed to be advantageous in that it would allow near complete reaction of the analyte precursor ions (full conversion) while preventing neutralization of singly charged product ions, preserve larger and relatively highly charged product ions as well as prevent production of the internal fragment product ions (ones that fail to include either the C- or N-terminal end of the original analyte precursor ion species). Such internal fragment product ions are produced by subsequent dissociations of first generation product ions. By "parking" the first generation ETD product ions, the product ion spectra would be more intense (sensitive) and more sequence information rich. Unlike for charge reduction reactions (IIPT/PTR etc.), the m/z values of product ions from ETD reaction are not known a priori if the m/z and Z of the precursor ions are known. Thus to effect suppression of subsequent reaction of first generation ETD product ion species the, ion parking has to be effected for product ions throughout a broad range of possible product ion m/z values which would include m/z's both above and below the precursor ion m/z.

In the McLuckey group paper, 2005 Chrisman et al, broadband product ion parking during ETD of peptide cation analyte precursors was described and demonstrated. The described work also resulted in a corresponding U.S. Pat. No. 8,334,503 (and other foreign counterparts). In 2005 Chrisman et al, a multi-frequency waveform was applied between the end caps of a 3D Quadrupole ion trap during the ETD reaction to inhibit further reaction of ETD product ions with reagent anions. (Note: In 2005 Chrisman et al the reagent anions are Nitrobenzene anions which are not particularly good ETD reagent anions—the partitioning between PT and ET reaction pathways is at least 50/50 in favor of proton transfer.) The multi-frequency waveform provided power over a wide range of frequencies would encompass the range of z-dimensional (by convention the axial dimension of a 3D quadrupole trap) characteristic frequencies of ion motion for the entire m/z range of product ions with the exception of relatively narrow notches (voids) in the power spectrum approximately centered on the z-dimensional characteristic frequencies of ion motion for the isolated precursor ion species and that of the reagent anions.

Figure 6A:
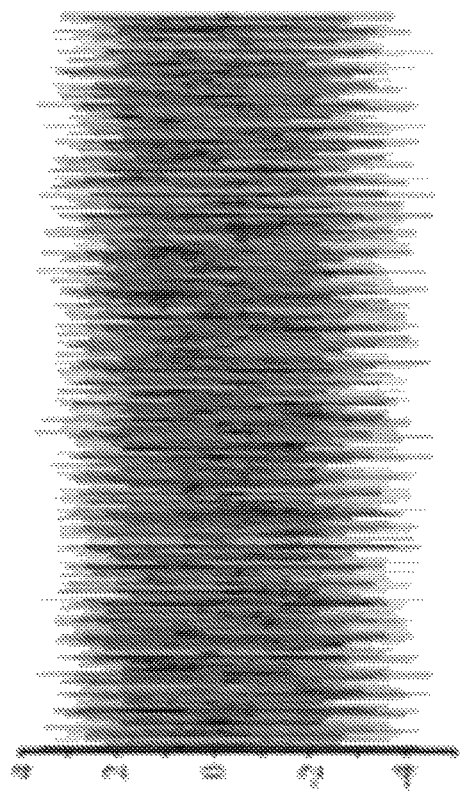
FIGS. 6A & 6B. Representations of the broadband parking waveforms described in the prior art.
Figure 6B:
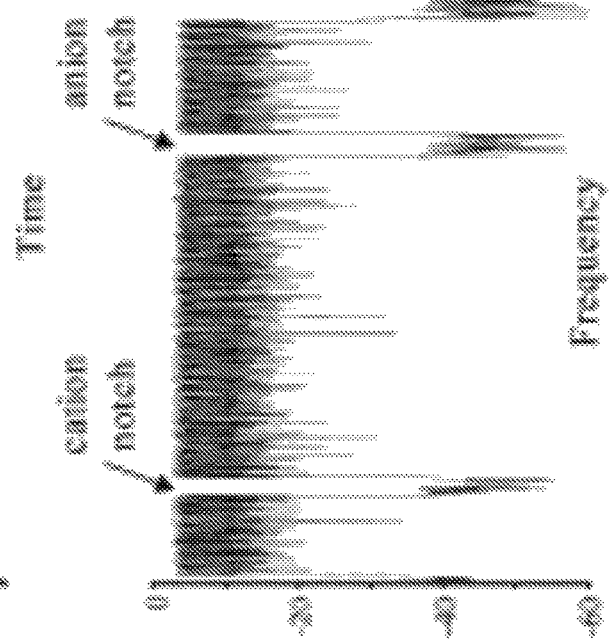

The particular type of multi-frequency (broadband) activation waveform utilized in accordance with this disclosure is called a Filtered Noise Field wave form. FIG. 6 is from 2005 Chrisman et al is an example of such a waveform (time domain) and its associated frequency spectrum. It is generated from digitized white noise (or pseudo/synthetic white noise) that that is filtered to have the observed notches in its frequency spectrum. The y axis is almost certainly in db (log scale). The intensity "voids" or "notches" the dipole waveform's spectrum are ~40 db lower than for the rest of the frequency range of the waveform. Note: 40 db is a factor of 100 on a linear (voltage) scale. In the frequency regions where there is waveform intensity, the intensity is not perfectly uniform. This is presumably because the pre-filtered waveform was white noise (or pseudo white noise) which on average has a uniform power spectrum but which, measured over a finite amount of time, will not have one. Such variation in frequency composition leads to variation in the kinetic excitation of ions of different m/z values since they have differing natural frequencies of motion. However the net excitation of ions of any particular m/z depends on the relative phasing and intensity of all the frequencies with the frequency components for the characteristic (natural) frequency of z-motion for that m/z. Those waveform frequency components closest to the characteristic (resonant) frequency of an ion's axial motion couple the most strongly.

The waveform shown in FIG. 6 would be expected to have provided fairly uniform kinetic activation for ions not having characteristic frequencies near or in the spectral "notches". ETD product ions that had m/z values that corresponded to z-axis characteristic frequencies that did not fall in or near the waveform notch bands, were kinetically excited quickly enough to produce suppressed ion-ion reaction rates (see discussion above). Those ion species that exclusively resulted from direct dissociation of the precursor ion (first generation reactions) were shown to have higher intensities (gains in intensity) when the parking waveform was applied during the reaction since they were not depleted by secondary ion-ion reactions. Since both the reagent ions and the original precursor ions have z-dimensional frequencies within the spectral "notches", they were only weakly or negligibly kinetically activated and the kinetics of their reaction was only slightly or negligibly reduced. Since the inhibition of the secondary ETD reactions of ETD reaction products was sufficiently effective, the time for reaction of the precursor could have been extended to make up for any reduction in precursor ETD reaction kinetics.

While the data in the Chrisman et al. are principally for ion-ion reactions of 3+ precursor ions $[M+3H]^{3+}$ (Angiotensin I, neurotensin and RKRARKE) with Nitrobenzene anions, the paper states that: "Gains are expect to be larger when this technique is applied to more highly charged reactant ions, as the difference in rate between the first reaction and subsequent reactions decreases, resulting in a lower maximum for first-generation products. In addition for larger systems the range of internal ions that could potentially be formed by sequential reaction increases greatly, further complicating interpretation of the spectra." The inventions described herein are improved methods to address practical difficulties encountered when the parking methods of the McLuckey group, including the broadband methods described Chrisman et al., are used for ion-ion reactions for protein ion having considerably higher charge states than those shown in Chrisman et al. These inventions stemmed out of an effort to utilize ion parking to enhance sequence coverage during MS/MS analysis of intact proteins using ETD followed by a step of IIPT to charge reduce the ETD products (ETD-IIPT).

Proteins are very long polypeptides and when ionized by Electrospray Ionization, readily ionize by protonation to high charge states. For example 20 kDa protein may protonate 25-30 times in an electrospray source (acidic conditions) resulting in a distribution of m/z peak envelopes (isotopic clusters) a m/z spectrum corresponding to various charge states of the same 20 kDA protein species. The degree of protonation for different proteins depends on a number of factors including, the overall length of the protein, the number of basic amino acids in the protein, the acidity of the spray solution. Generally, only a single charge state/isotopic cluster is m/z selected as the precursor ions for dissociation in an MS/MS experiment. However, the precursor window m/z selection window may be chosen to be sufficiently broad embrace the isotopic envelopes of multiple charge states of the same species. Alternatively sequential precursor m/z selections (if precursor selection is performed in a separate device from that used for the ion-ion reaction) or multi-m/z isolation methods (if the m/z selection occurs in the same device as the ion-ion reaction) may be used to m/z select a precursor ion population composed of multiple charge states of a protein for collective reaction and/or dissociation. When protein ions undergo a single ETD reaction, these reactions can result in a very large number of possible product ions. These include the characteristic c- and z-type as well as the less abundant a- and y-type product ion series. Such sequence ions are produced by cleavage of bonds on the amino acid backbone of the protein (sequence ions) and most all amino acids on the protein ions are subject to dissociation. Additionally, ETD, like Electron Capture Dissociation (ECD), produces product ions associated with bond cleavage in the side chains of certain amino acids. These product ions are not sequence diagnostic but can represent significant fraction of the types of product ions produced by an ETD reaction. Further, ETD product ions from proteins can have molecular weights of the many thousands of Daltons. When the cleavage occurs relatively close to one of the termini of the protein, the larger of the product ions will have a molecular weights and charge states such that their m/z will be distributed around the m/z of the precursor ion. Larger product ions produced by dissociation at the same amino acid (position on the protein backbone) will be produced in multiple charge states. For a given charge state of any given large product ion species the ion signal be distributed among many isotopic peaks thus reducing the signal-to-noise ratio for any individual product ion m/z peak. Hence it is strongly advantageous to build product ion spectra from as many detected ions as possible, as the higher the number detected ion number, the better represented will be the lower abundance product ion species in the product ion m/z spectrum and thus yield a fuller representation of the full range of sequence ions produced (more sequence coverage).

The high charge states of protein ions generated by ESI, lead to very high reaction rates for precursor ions with the singly charged reagent ions. It is well established in the literature theoretically (1998 McLuckey and Stephenson) and confirmed experimentally, that ion-ion reaction rates vary as the product of square charge states of the analyte and reagent ions. In the conventional three segment RF linear quadrupole trap devices (see 2004 Syka et al) where the standard reagent populations for ETD reactions are such that a 3+ peptide precursor m/z peak would deplete to 10% of its original intensity in 50 msec, a 30+ precursor protein would be expected to react 100 fold faster and be depleted to 10% of its initial intensity in 0.5 ms. In practice with the 3 segment traps which were used for the experiments that led to the inventions described herein, the reagent and analyte precursor ions are kept in separate sections of the trap before charge state independent trapping is effected and the cations and anions are allowed to mix and react. The mixing time is probably on the order of 0.5-1 msec, so accurate control of the reaction by control of the reaction time (under static reaction conditions) to this level is not really available. One can certainly set the reaction time to 0.5 msec but the mixing of anions and cations will not be complete, so automated prediction and control of the completeness of the reaction would be difficult. Reducing the population of reagent ions can reduce the rates of reactions as reaction rates are nominally proportional to the density of reagent ions to which precursor ions are exposed. However reduction in the reagent population causes certain practical difficulties, as lower reagent populations can lead to the kinetics of the reactions no longer be pseudo first order, which greatly complicates the automatic control of reaction completeness via control of reaction time. Further, in RF QLT type reaction cells lower reagent populations can lead to difficulties in getting to the reagent and analyte ions to mix. It is believed that small amounts of surface charge on the QLT electrodes can cause axial segregation of precursor and reagent ions. Such surface charge induced axial potentials are overcome by the space charge potential of sufficiently high populations of reagent ions When dissociation of the protein precursor ion occurs near (in a relative sense) to either the C or N termini of the protein, the resulting large (in mass) analyte product ions will almost certainly have a very high charge states and such products thus will still have very high (secondary) reaction rates with the reagent ions. Charge not consumed by a single ETD reaction will be distributed to the resulting product ion pair approximately according to their length. This assumes that number of basic amino acid residues in each generation product is approximately proportional to the length of the product ion. While certainly the number basic amino acid residues in each product ion species (which is protein specific) will affect this portioning of the charge between products, this simple model qualitatively predicts what is observed in real ETD product ion spectra of protein cations. Unless something is done to inhibit the exposure of first generation product ions to further reaction (ie. ion parking), the reaction conditions that will cause substantial depletion of the precursor ions in the chosen reaction time will also result in most large (highly charged) first generation product ions to also undergo ion-ion reactions.

For example a product ion that is has 90% of its precursor species mass, would be expected to have rate constant for reaction with the ETD reagent ions of ~81% of the precursor species. Thus long first generation product ions from protein precursor ions are depleted in the resulting product ion spectrum unless something is done to inhibit their further reaction with ETD reagent anions. When a first generation product ion undergoes further dissociation along the protein backbone it generates a C- or N-termini contain product (a shorter sequence ion) and an internal fragment ion. The internal fragment m/z peaks do not contribute information useful in sequence identification. The number of different possible internal fragment species is much larger (by a large multiple) than then number of N-terminal and C-terminal sequence ions. This means the internal fragment signal is distributed across a very large number of product ion species (structures and charge states). Such internal fragment ions have low signal-to-noise ratio and that they are spread almost continuously throughout m/z range where the sequence N- and C-terminal sequence ions appear. They are observed in the product ion spectrum as sort of a base line or "hash" of "chemical" interference or "noise". Internal fragment ions represent a repository for charge (signal) from the precursor ions. Depending upon the reaction conditions (reagent ion number, reaction time etc.), the ETD product ion spectra of proteins can be composed of product ions of several generations of ETD reactions as the largest (longest and therefore likely to be most highly charged) product ions in each generation react quite quickly. The longer ETD reactions are allowed to proceed without m/z selective inhibition, the distribution N- and C-terminal sequence ions (primarily c- and z-type) becomes progressively biased toward shorter and lower charge state product ion species and more of the total ion signal (charge) is devoted to internal fragment ions not sequence ions.

IIPT (PTR) reactions on protein ions and/or product ions (of any generation) from dissociated protein ions pose somewhat different challenges. If the IIPT reaction is performed directly on protein precursor ions, the objective may be to enable gas phase purification of protein ions. For samples that are complex mixtures, in even a relatively narrow window of precursor m/z selection there may be several different protein and peptide species having different charge states. IIPT disperses these peaks into different charge states and m/z values. IIPT reactions using conventional singly charged IIPT reagent anions result exclusively (at least for practical purposes) in charge reduction and no dissociation products (from covalent bond cleavage) are observed. However IIPT does have the potential to remove adducted solvent molecules from the protein, making the IIPT product ion spectra relatively free of m/z peaks from solvent adducted protein ions, improving the ability to assign m/z and therefore molecular weight from the distribution of isotopic clusters associated with the charge state of proteins present. When the m/z analyzer has insufficient resolution to permit determination of the charge state of the ions in an isotopic peak cluster by their m/z separation, IIPT can be used to generate multiple reduced charges states of the precursor ion. The resulting product ion m/z spectrum then consists of a multiplicity of isotopic cluster m/z peaks corresponding to a series of reduced charge states of the precursor protein or proteins from which, the charge state and, the molecular weight of the protein or proteins can be determined.

The rate constants for of IIPT reactions, are also proportional to the product of the square of the charge states of the analyte ions and the reagent ions. IIPT product ions are restricted to analyte product ions species of that are reduced by one unit charge from that of the precursor ion. The mass of the product ion is reduced by the mass of a proton (typically) or by the loss of a proton and, in some instances, the mass of a solvent molecule that had been non-covalently adducted to the precursor ion and detached by the IIPT reaction. Thus, absent m/z selective inhibition of the subsequent IIPT reactions (ion parking), the products ions from a single a IIPT reaction of a will be quite high and exposure of the protein precursor ions to reagent ions sufficient to substantially deplete the precursor ions will also lead to the product ions also undergoing charge reduction via IIPT reactions. Generally because the kinetics for further IIPT reactions of each generation of product ions are high, such reactions produce a multiplicity of reduced charge state product ion species. An example of this is shown in FIG. 7A which shows an experimentally obtained product ion mass spectrum from IIPT of the 26+ charge state, $[M+26H]^{26+}$, of Apomyoglobin (10 ms IIPT reaction time). The most abundant product ion species is the 12+ charge state, which is the result of 14 consecutive IIPT reactions with the perflouromethyldecalin (PFMD) reagent ions.

In the context of gas phase purification types of IIPT experiments, ion parking is useful in that it allows the IIPT products of a targeted protein to be concentrated in a one or a very few product ions. Such "purified" and concentrated IIPT product ions can then be subjected to other manipulations including m/z selection and dissociation. Alternatively, if unknown species are involved, ion parking can be used to prevent IIPT product ions from being charge reduced to such an extent that their m/z is beyond the useful (or optimal) m/z range of the instrument.

IIPT is also useful in the in the charge reduction of ETD product ions (as well as for product ions produced by other ion dissociation methods appropriate for dissociating protein ions, such as UV or IR photo dissociation, various forms of collision induced dissociation etc.) as first generation products of a precursor protein ions will often have m/z values that are close to the m/z the precursor. If the charge on a protein precursor ion is reasonably evenly distributed along the protein, cleavage at most points along the backbone will produce product ions that have m/z that are similar to that of the precursor. This makes for a very dense/complicated product ion spectrum in the general neighborhood of the precursor ion m/z. The isotopic distributions of many different dissociation products can overlap making m/z and charge state assignment very challenging. Subjecting such product ions to IIPT reactions spreads the product ions to higher m/z and over a wider m/z range. This reduces the m/z spectral peak density and facilitates correct automated m/z and charge state assignments. In some cases it is advantageous to m/z select a window of dissociation products ions and then subject them to Tin in order to reduce overlapping of the isotopic peak envelopes in the product ion spectrum. This accomplished in our apparatus by applying an auxiliary dipole field waveform m/z isolation step between the ETD and IIPT steps and would constitute an $MS^3$ type of experiment.

For IIPT reactions subsequent to ion dissociation, ion parking methods allow the analyst to control how high in m/z the IIPT product ions will be charge reduced to. The goal generally is to distribute the ETD/IIPT product ions more widely throughout the useful range of the m/z analyzer and have little product ion signal in ions above the useful m/z range of the analyzer. Since the kinetics of IIPT are charge state dependent (varies as the square of the analyte ion charge state) effective ion parking also can prevent the over reduction in charge of really high charge state product ions putting them above the useful m/z range of the analyzer as well as their dispersion into too many charge states, whilst still effecting charge reduction of the lower charge state species.

The instrument that was used for the experiments that led to the described inventions was a modified hybrid RF QLT—Orbitrap instrument originally manufactured by Thermo Fisher Scientific. The LTQ Orbitrap Velos Pro ETD system (eventually upgraded to be an LTQ Orbitrap Elite ETD by changing the Orbitrap analyzer and software) was modified to have a front end ETD reagent ion source (a prototype combined atmospheric pressure ionization inlet and reagent ion source from an Thermo Fisher Scientific Orbitrap Fusion instrument). This instrument has a dual cell QLT placed ahead of the Orbitrap analyzer in the ion path. This arrangement enables product ions from the multiple cycles of precursor ion accumulation-precursor ion isolation-ion manipulation (including ion-ion reactions) to produce product ions in the high pressure cell of the dual cell QLT to be sent to and accumulated in the C-Trap (or HCD cell) and then analyzed collectively in the Orbitrap. This improves the signal-to-noise ratio of the product ion spectra as the total number of ions (and charges) that are detected in each spectrum is much greater.

The ion-ion reactions are performed in the high pressure cell of the QLT (HPLT). During the ion-ion reactions a second RF voltage is applied to the end plate lenses of the high pressure cell of the HPLT (the front and center lenses of the dual cell QLT assembly) and the DC voltages applied to the end plate lenses and sections of HPLT are all made equal (to the precision of the control of output of the amplifiers that supply these voltages). The end lens RF voltages provides axially confining pseudo-potential barriers at the ends of the QLT for both the analyte and reagent ions (opposite polarity) while the absence of imposed DC axial gradients permit the reagent and analyte ions to be co-trapped along central (neutral) axis of the device. The basic procedure is described in U.S. Pat. Nos. 7,026,613 and 7,534,622, as well as in 2004 Syka et al. and 2004 Coon et al. A minor distinguishing feature of the particular modified system was that both the reagent and analyte ions enter the QLT from the same end of the device.

The inventive methods described herein came out of an effort to apply the McLuckey group's broadband parking methods to ETD of intact proteins on the modified LTQ Orbitrap Velos ETD. The goal was to preserve the large ETD product ions by limiting the observed analyte product ions to those produced by a single electron transfer ion-ion reaction. A another objective was to use ion parking to control IIPT reaction of ETD product ions for reduction the charge of ETD product ions so as to reduce the spectral overlap of ETD product ion m/z peak by charge reduction whilst ensuring that m/z charge reduced product ion species remained within the m/z range of the instrument. A further objective was to improve m/z selective ion parking for IIPT reaction products for purposes of gas phase ion purification of protein and polypeptide ions.

The instrument control software functions for calculation of m/z isolation waveforms were re-purposed to calculate the broadband or multi-band ion parking voltage waveforms and load them into the instruments the instruments digital waveform memory. The instrument control code was then modified to produce these stored ion parking waveforms as voltages via the instruments arbitrary voltage waveform generation circuitry, amplify them and apply them between the opposing rod electrodes (all three segments of the x rod pairs) of the HPT during ion-ion reactions. The applied voltage waveform thus superposed a corresponding AC dipole field on to the 2D RF quadrupole trapping field during the ion-ion reactions.

The multi-frequency broadband voltage waveforms which are applied between opposing electrodes of 2D and 3D RF quadrupole trap devices built by Thermo Fisher Scientific (and its predecessor organizations) for purposes of ion m/z selection (including isolation) and, in this case, ion parking, are somewhat differently composed than the filtered noise (or pseudo-noise) waveforms used by McLuckey group in their original work on broadband ion parking. The waveforms are calculated as a truncated Fourier (harmonic) series of frequency components having defined amplitudes of with the relative phasing of the frequency components varying as a quadratic function of frequency. The U.S. Pat. No. 5,324,939, describes principles underlying the generation these waveforms. The examples given in the patent are for 3D ion traps but the underlying principles for the composition of the waveforms for m/z isolation remains substantially the same for the RF QLT analyzers in both the Thermo Fisher Scientific LTQ series instruments and the TFS Orbitrap Fusion series instruments. Typically, the waveforms have a period of 2 ms and thus have a frequency spacing of 500 Hz. The synthesizer clock rate is 2 MHz. The nominal frequency of the RF Quadrupole trapping field is 1.15 MHz, so after the requisite filtering of the synthesizer output, amplification and coupling to the trap electrodes, the instruments waveform generation and amplification circuitry is able to cover the entire range of ion lowest order resonant natural frequencies of ion motion from below 10 KHz to above 575 KHz. This covers most all of the practical range for trapped ion natural frequencies. In the normalized frequency domain of the Mathieu equation and its solutions, this correspond to the range for normalized ion characteristic frequency, $\beta$, from below $\beta=0.0174$ to $\beta=1$ (the stability limit).

While the teachings of U.S. Pat. No. 5,324,939 are directed to m/z selection while ions are being introduced into an ion trap, the disclosed concept of temporal spectral homogeneity is very relevant in the construction of broadband ion parking waveform. For broadband ion parking it is advantageous to have as much temporal uniformity in the kinetic activation the ions within the m/z ranges (frequency ranges) to be parked as is physically allowable. While it is impossible to create waveforms continuously provide kinetic excitation to broad ranges of trapped ion m/z values with uniformity at all times, the teachings U.S. Pat. No. 5,324,939 provide guidance to construct parking waveforms that will provide kinetic excitation to all trapped ion m/z values within the desired range for parking with sufficiently regular kinetic excitation such that they remain sufficiently excited such that their rate for undergoing ion-ion reaction is effectively suppressed.

The key observation that led to the inventions described herein was, in part, serendipitous and occurred during the inventors initial attempts at constructing and utilizing McLuckey group style broad band parking waveforms during ETD and PTR of protein precursors ions, wherein there were deliberate voids (notches) in the parking waveform spectral intensity in the frequency ranges about the frequencies of the m/z isolated protein precursor ions and the frequencies of the m/z isolated reagent anions. Parking waveforms such as shown in FIG. 6 and its associated frequency spectrum are shown with notches. The purpose of such spectral "notches" was to prevent significant suppression of the kinetics of the ion-ion reactions between the precursor ions and the reagent anions by minimizing the activation of ions in of the neighborhood of the m/z values of the precursor and reagent ions whilst still kinetically activating product ions having m/z values not close to those of the precursor and product ions in order to suppress their reaction rates and thereby effect product ion parking for such product ions. Inexperience with the instrument software waveform construction tools led to the accidental construction and use of ion parking waveforms that had significant intensity in the frequency ranges where there should be effectively none (the "notches") thus providing some non-negligible degree of kinetic activation of precursor and reagent ions. When it was determined that frequency composition of these "first" parking waveforms were not as intended, the instrument control software code was written to generation of broadband parking waveforms where there was negligible spectral intensity in the spectral "notches" around the frequencies corresponding to the m/z values of the precursor and reagent ions. However when such "corrected" parking waveforms, which were constructed according to the teachings of the McLuckey group, were applied during ion-ion reactions they were demonstrably less effective at parking high charge state product ions. In comparable experiments, with experimental parameters optimized for each type of parking waveform, of the "first" type of parking waveforms consistently produced more complete parking for highly charged product ions than the "corrected" type of parking waveforms. This unexpected and unanticipated result lead to many further experiments by which it was determined that critical difference between the "corrected" type and the "first" type of activation waveforms was the non-negligible intensities for frequencies within the "notch" or "void" band in the parking waveform corresponding the range of frequencies associated with the reagent ions.

These experimental results have led to a simplified and qualitative model or understanding of the processes involved ion parking that has been a useful tool in the conception of the various novel methods for ion parking that are described herein. The kinetic activation of the reagent ions reduces the kinetics of ion-ion reactions for all analyte ions (both precursor and product ions). For a product ions having a m/z within the range of m/z values subject to kinetic activation by the application of the parking waveform (thus having a m/z within an intended m/z window for parking), there is an interval of time between when the product ion is created via an ion-ion reaction and when it achieves a sufficient level of kinetic activation and correspondingly large oscillatory trajectory to effectively shield it from further reaction—a "spin up time"—during which the product ion is vulnerable to further ion-ion reaction and conversion to a lower charge state species or dissociation into other lower charge state ion species. The probability that a further reaction will occur is dependent upon the rate at which the kinetic energy and correspondingly, the ion's oscillation amplitude increase due to the action of the parking waveform, and the "base" rate of ion-ion reaction for that ion with the reagent ions. The "base" rate of ion-ion reaction for the product ion would be its reaction rate in the absence of kinetic activation by anything other than collisions with background gas molecules and the principle confinement fields. If the ion-ion reaction rate is quite high during that initial "spin up" time then there is a good probability that the analyte will undergo a ion-ion reaction even though it should be "parked". Mild kinetic activation of the reagent ions by the frequency components of the parking waveform close to the one of the resonant frequencies of the reagent ion, slows the kinetics of ion-ion reactions for all of the analyte ions (precursor ions, any intermediate product ions and product ions within the parking activation region). This occurs because, as described by McLuckey and co-workers (1998 McLuckey and Stephenson, 2002 Reid et al.), the rate constants for ion-ion reactions has a $v^{-3}$ dependence, where v is the differential velocity between the reagent and analyte ion species. Kinetically activating the reagent ions increases the differential velocity between all analyte ions and the reagent ions. Also kinetic activation of the reagent ions increases their oscillation amplitudes in the RF trapping field and thus, in a temporal average sense, the reagent ion cloud size, and therefore reduces the density of the reagent ions that the analyte precursor and product ions experience. The probability that an individual analyte product ion undergoes an ion-ion reaction thus depends upon the density and relative velocity distribution of the reagent ions it is immersed ion. Unless the product ion has a m/z close to that of the reagent ions (and this is generally not the case), kinetic activation of the reagent ions does not alter the "spin up" time for newly created charge reduced product ions. Instead the kinetic activation of the reagent ions reduces the reaction kinetics for the charge reduced species within the parking band sufficiently so that during the "spin up" time the analyte product ions have a much lower probability of reaction. According to this qualitative model, inefficient ion parking for large product ions from proteins ion precursors is due to the very high reaction rates for these highly charged species. Activation of the kinetic activation of the reagent ions is an effective way to reduce these reaction rates for without having to resort reducing the reagent ion population which would be disadvantageous.

The effect of mild kinetic activation of reagent ions on the reaction rates with highly charged analyte ions demonstrated in FIG. 7B which shows the experimentally obtained product ion mass spectrum from IIPT of the 26+ charge state, $[M+26H]^{26+}$, of Apomyoglobin (10 ms IIPT reaction time) where the reagent ions are subject kinetic activation during the ion-ion reaction period. The most abundant product ion species is the 18+ charge state, which is the result of 8 consecutive IIPT reactions with the perflouromethyldecalin (PFMD) reagent cations. In comparison to the result in FIG. 7A for the identical experiment except without kinetic activation it is clear that the reaction rates for all generations of reactions are considerably reduced.

The qualitative model described above would predict that modest kinetic activation of the precursor ions would both slow down the reaction of highly charged precursor ions and facilitate parking of first generation products. Further, this qualitative model would also suggest that for m/z selective ion parking during non-dissociative charge reduction ion-ion reactions such as IIPT, modest kinetic activation of the intermediate ion species of charge state one higher than charge state, Z, of the m/z of the product ions that are intended to be parked—the immediate precursor species of product ion to be parked—might also be advantageous. Here it is understood that this modest kinetic "pre-activation" should not be sufficient to cause ion ejection or to induce dissociation by collisional activation. The purpose of the modest kinetic activation of precursor or intermediate precursor ions would be to kinetically "pre-activate" these ions such that, upon their creation, the product ions intended to be parked would have thus already have a degree of kinetic activation that they would inherit from their precursor species. This kinetic "pre-activation" could be expected to shorten the "spin up" time for first generation product ions within the m/z range for parking determined by the applied parking waveform. The authors of this specification have yet successfully demonstrate that, in the absence of kinetic activation of the reagent ions, kinetic activation of the precursor ions or intermediate product ions that are the direct precursor of product ions within the ion parking m/z window improves the effectiveness of ion parking of highly charged product ions. This may be in part due to the specific configuration and operational aspects of the RF QLT used for the experiments. Also such kinetic pre-activation may be less effective in enhancing ion parking than anticipated because the oscillatory motion (kinetic activation) inherited from the precursors (primary or intermediate product) by product ions may often have phase relative to the motion imparted by the parking waveform such that the collective result may be that the product ions are kinetically deactivated before they become kinetically activated—product ions will sometimes be "spun down" before they are "spun up"—thus exposing the product ions to further ion-ion reaction before they achieve sufficient kinetic activation to effectively "park" them. In any case, modest kinetic activation—kinetic activation insufficient to cause dissociation or ejection—of precursor ions or intermediate product ions by frequency components of an applied parking waveform, in conjunction with mild activation of the reagent ions by other frequency components of the parking waveform to enhance parking of ions within a defined m/z range for parking should be considered within the inventive scope of this specification.

In this specification, the phrase mild kinetic activation is used to describe the degree of kinetic activation of reagent ions that is sufficient to reduce the rate constant of to reduce the kinetics of ion-ion reactions of the reagent with ion species within the m/z range of ion parking determined by the frequency and amplitude composition of the parking waveform field. The degree of activation required will depend on a number of variables. An excessive kinetic activation can cause reagent ions to be ejected from the device and thus be lost. Further, an excessive kinetic activation may cause the reagent ions to undergo dissociative collisions with the background buffer/damping/collision gas molecules. Such dissociative collisions can result in product reagent ions that are of m/z that are not stably trapped and thus are ejected from the trap. Stably trapped reagent product ions, may have various different m/z values and thus will subject to different levels of kinetic activation. Such trapped reagent dissociation product ions may react faster or slower than the "precursor" reagent ions. In the m/z of dissociation product ions may be outside the intended activation m/z window for reagent ions resulting in much higher than anticipated reaction rates with analyte ions. This would defeat the purpose of kinetic activation of the reagent ions. Also, the ETD reagent anion species, because of their proclivity to donate electrons will readily undo electron detachment when moderately collisionally activated.

For these and many other reasons there are upper limits on the degree of kinetic activation that that reagent ions can be subject and be practically useful. The range of kinetic activation that should be construed as mild as it is meant herein would in general vary depending upon the specifics of dimensions, operating frequency, and magnitude of the trapping field voltages applied to the ion-ion reaction cell electrodes as well as the specific reagent ions species utilized for the ion-ion reactions, the type and pressure of the buffer/damping/collision gas and of the specific method of kinetically activating the reagent ions. Herein, mild kinetic activation of reagent ions should be construed as activation sufficient to produce reduction in rate constant for reaction with analyte ions to less than 70% of what it would be if the reagent ions were not subject to such activation and that no more than 10% of this reduction in the reaction rate is due to reagent ion loss due induced by kinetic excitation as described above.

For modes of this invention where kinetic activation of the reagent ions is accomplished by applying auxiliary single or multi frequency waveform potentials to the reaction cell electrodes, the kinetics of the ion-ion reactions can be measured for the cases where the only difference is that the applied waveform potentials either include do not include the frequency components that are specifically incorporated in the waveform in order to kinetically excite the reagent ions. Monitoring the rate of depletion of precursor analyte ions as function of reaction time in series of experiment where nominally identical experiment differing only in the ion-ion reaction time enables measuring of the rate constants. When suitably large populations of reagent ions are used relative to the precursor ion population, the ion-ion reactions behave in good approximation according to pseudo-first order kinetic theory and the abundance of the unreacted precursor ions with reaction time will decay approximately exponentially. Reaction rate constant can be derived from a fit of this data to an exponential function. In experiments where the reagent ions are subject to kinetic activation, that the precursor ion abundance with reaction time is well modeled as exponential decay is alone evidence no loss of reagent ions as a consequence of their kinetic excitation from the waveform field. Confirmation that reagent ions are not significantly lost or dissociated during the ion-ion reactions because of the application of the waveform potential can be accomplished performing all the steps of a desired ion-ion reaction experiment but without introducing analyte ions and instead of analyzing and detecting the analyte ions, detecting and analyzing the remaining reagent ions. The m/z spectrum of the reagent ions will indicate the growth of significant abundances of dissociation products of the reagent ions nor a depletion of reagent ion abundance when the ion-ion reaction period is extended through the range normally used when analyte ions are present. Since reagent ion numbers can be quite high in relative to analyte ion abundances it may be necessary to either lower the reagent ion numbers or reduces the gain of the ion signal detection system in these experiments.

Figure 15:
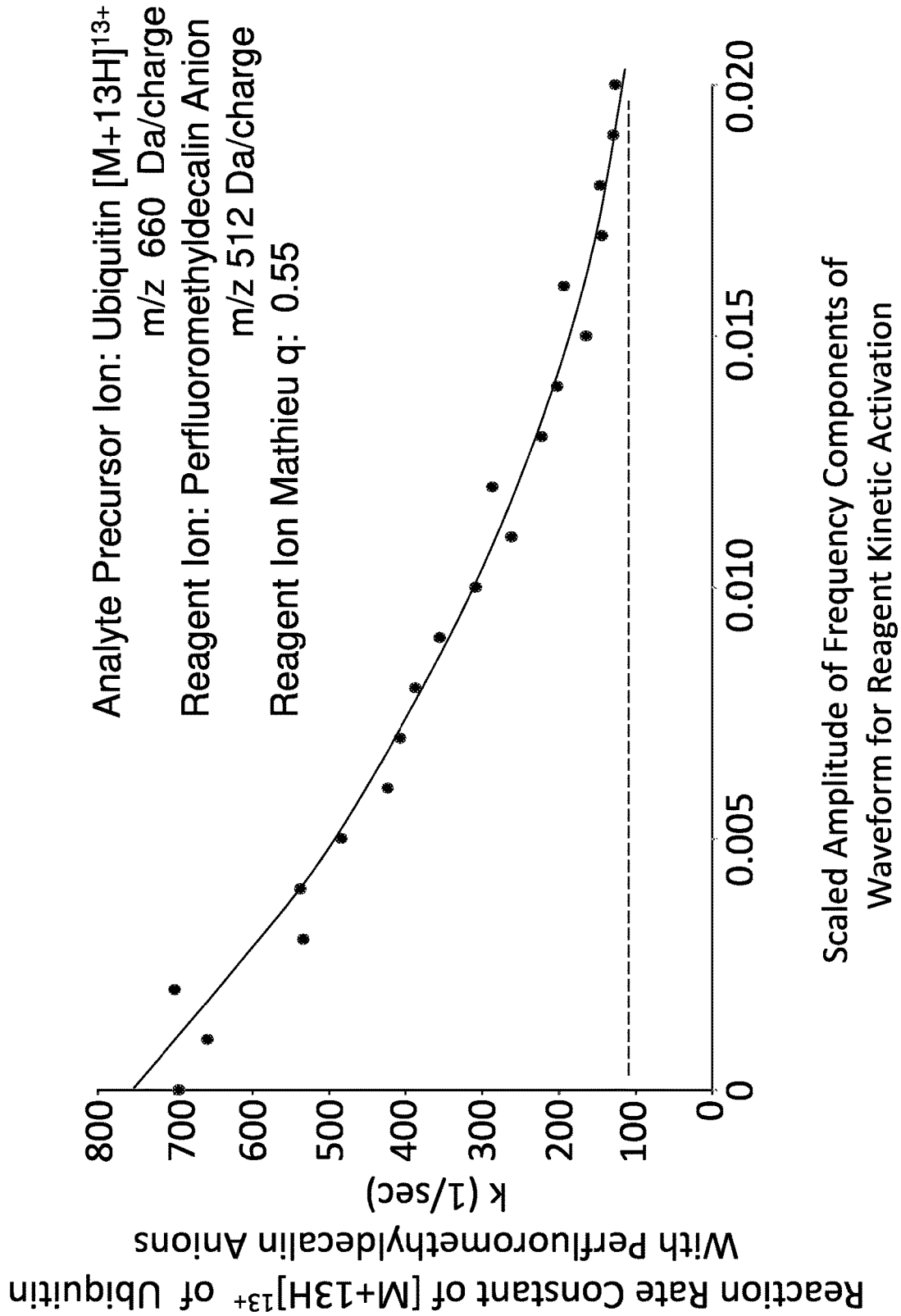
FIG. 15 Plot of experimentally determined dependence IIPT reaction rate constant, k, of [M+13H]13+ of Ubiquitin with Perfluoromethyldecalin Anions (m/z 512 in the high pressure cell of the dual cell QLT on the amplitude of the parking waveform frequency components used for kinetically activating the reagent ions.

An example of the effect of reagent activation on ion-ion reaction rate constant is illustrated in FIG. 15. In this figure, the experimentally determined rate constant, k, of reaction (IIPT) of the 13+ charge state of Ubiquitin, $[M+26H]^{26+}$ (m/z 660 Da/elemental charge), with PFMD reagent anions is shown as a function of the amplitude of the band of dipole waveform frequency components for kinetic excitation of the PFMD reagent ions. The RF trapping field voltages were such that the Mathieu q for the PMD reagent ions (m/z 512 Da/unit charge) was 0.55 during the IIPT reaction period. The amplitude of the frequency component of the waveform is expressed in the normalized units used in calculating the parking waveform and are proportional to the actual amplitude of the applied waveform voltage frequency components applied to the opposing electrodes of the linear trap. In the case the waveform consisted of only frequency component appropriate for kinetic activation of the reagent ions. The rate constant, k, for each level of reagent excitation was determined by fitting and exponential decay function to the abundance of the remaining precursor ion, Ubiquitin 13+, for a series of MS/MS IIPT spectra where the IIPT with progressively extended reaction times. Initial precursor and reagent population, within the limits of experiment variability, were the same for all experiments. The data in FIG. 15 indicated that activation of the reagent ions progressively reduced the reaction rate constant for the reagent—analyte precursor ion-ion reaction from its initial "base" value. At the maximum degree of reagent activation, the rate constant was reduced to about $\frac{1}{7}$ of its "base" value. This demonstrates that the ion-ion rate constants can be controlled by the degree of reagent activation. This is only an illustrative example. The range of control of the reduction in reaction rate constant will depend on many parameters including the reagent ion species and it susceptibility to dissociation or charge detachment, the trapping conditions such as RF frequency, the Mathieu q the reagent ions at which the ions are maintained during the reaction, the damping/collision gas, and finally the m/z and charge state of the analyte ions. Through appropriate calibration of the kinetics of ion-ion reactions with various degrees of reagent activation in a particular apparatus or instrument, it is technically feasible and desirable to provide automatic control ion-ion reaction kinetics both for MS experiments that involve ion parking an those that do not.

FIGS. 8A & 8B demonstrate the improvement in the effectiveness in ion parking when in accordance with the invention, kinetic activation of reagent ions, is incorporated in to an ion-ion experiment. Two product ion m/z spectra from IIPT ion parking experiments wherein the precursor ions species is the 26+ charge state, $[M+26H]^{26+}$, of Apomyoglobin are shown. The reagent anions are the radical anions of PFMD (m/z 512 Da/unit charge) and held at Mathieu q of 0.55 during the reactions. In the scan experiments that produced these spectra, the charge reduced product ions within the m/z range indicated by the shaded region of the spectra (approximately 1500-2250 Da/unit charge) where activated by a band of frequencies in a dipolar parking waveform applied as shown schematically in FIG. 2. These experiments only differ in two respects. In the scan experiment that produced the spectra in FIG. 8A (a scan experiment in accordance with the prior art) there were no frequency components for reagent activation in the parking waveform. A 10 ms IIPT reaction period was required to achieve the eleven or more consecutive charge reduction reactions to produce the m/z peaks within the range for ion parking. While the large difference in of intensity the charge reduced apomyoglobin 12+ and 11+ m/z peaks indicates that the parking waveform greatly slows the rate of reaction for charge states within the parking window—the 12+ charge state is almost completely absent from the spectrum—the reduction rate is not sufficiently high so as to suppress further consecutive charge reduction reactions as m/z peaks from the 10+, 9+ and 8+ charge states of apomyoglobin are observed in high relative abundance. The intensity of the applied parking waveform was such that further increase would begin to subject product ions within the parking m/z window to dissociation or ion ejection. In the scan experiment that produced the spectrum in FIG. 8B was one in accordance with one mode of the invention, wherein a band of frequencies was added to the ion parking waveform specifically to provide mild kinetic activation of the reagent ions. In FIG. 8B the m/s peak corresponding to the 11+ charge state of Apomyoblobin is both the most intense m/z peak and it comprises approximately 85% of the ion signal in the spectrum. The 10+ charge state m/z peak has an abundance that is less than 5% of that of the 11+ charge state m/z peak, indicating further IIPT reactions of the 11+ charge state were substantially arrested effectively "parking" the sequence of charge reduction reactions at the 11+ charge state of the analyte. Since the reagent kinetic activation slowed the reaction rates for all the analyte ions (precursor and charge reduced products) the reaction time was extended to 120 ms to achieve this result.

Figure 9:
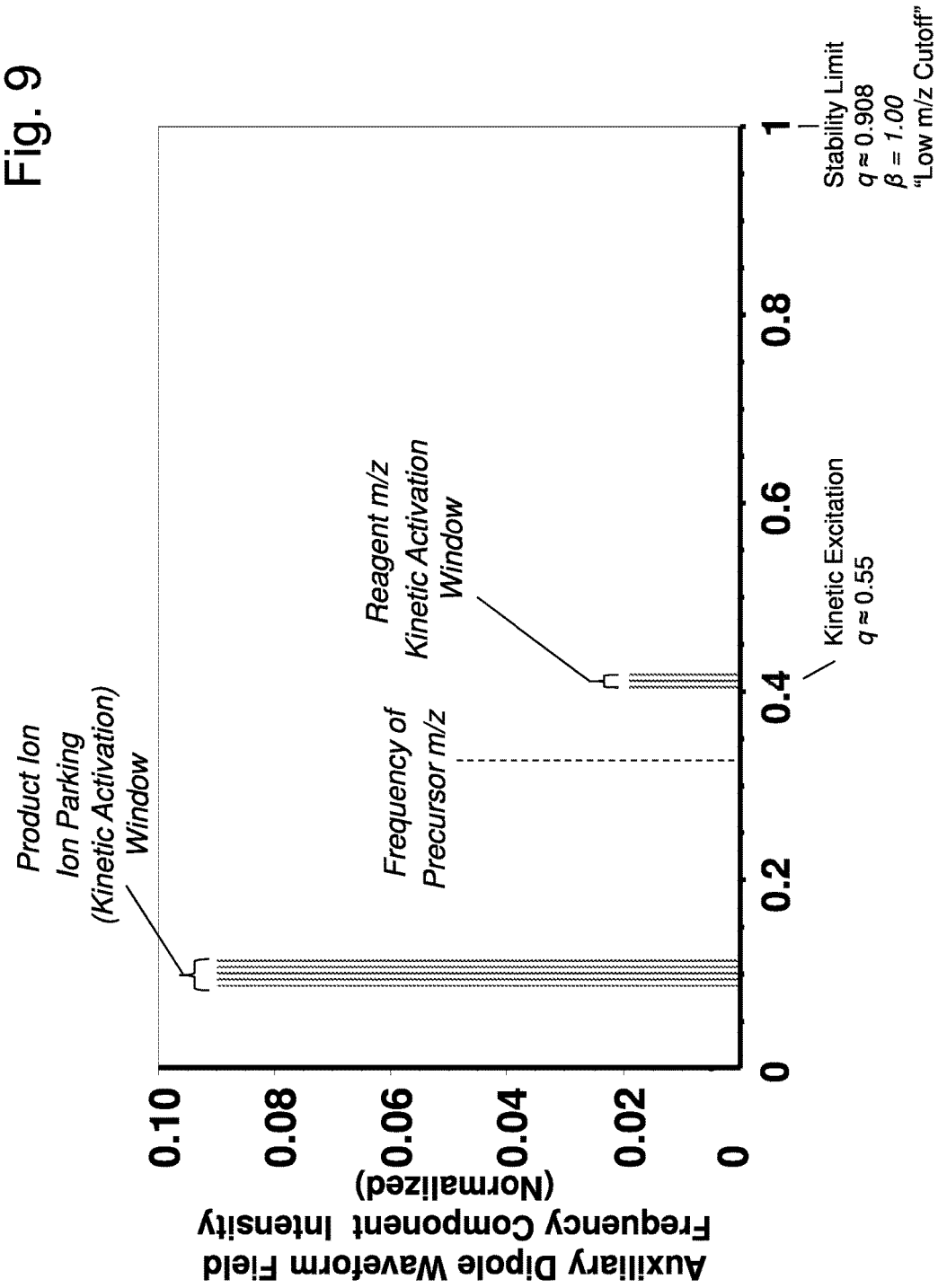
FIG. 9 An illustration of the frequency composition (Mathieu normalized) of a parking waveform in accordance with the one embodiment and used to produce the m/z spectrum in FIG. 8.

FIG. 9 is illustration of the frequency composition of a parking waveform in accordance with the one mode of the invention and used to produce the m/z spectrum in FIG. 8B. This figure and all such figures depicting waveform frequency composition shown herein are meant to teach the general features of waveforms and not to be exact representations of parking waveforms. These figures show the waveform component frequencies expressed on the normalized scaling of the standard form of the Mathieu equation and its solutions. In this scaling for a given true waveform frequency component of having angular frequency, $\omega_{aq}$, the corresponding Mathieu normalized waveform component frequency is $\alpha_{aq}$, where $\alpha_{aq}=2\omega_{aq}/\omega$ and $\omega$ is the angular frequency of the RF trapping field. FIG. 9 shows bands of waveform component frequencies for kinetic excitation of the charge reduced analyte product ions and the reagent ions respectively. The intensity of these bands match the numerical intensity used in calculation of the waveforms of the scan experiments that produced the spectra in FIG. 8.

Figure 10:
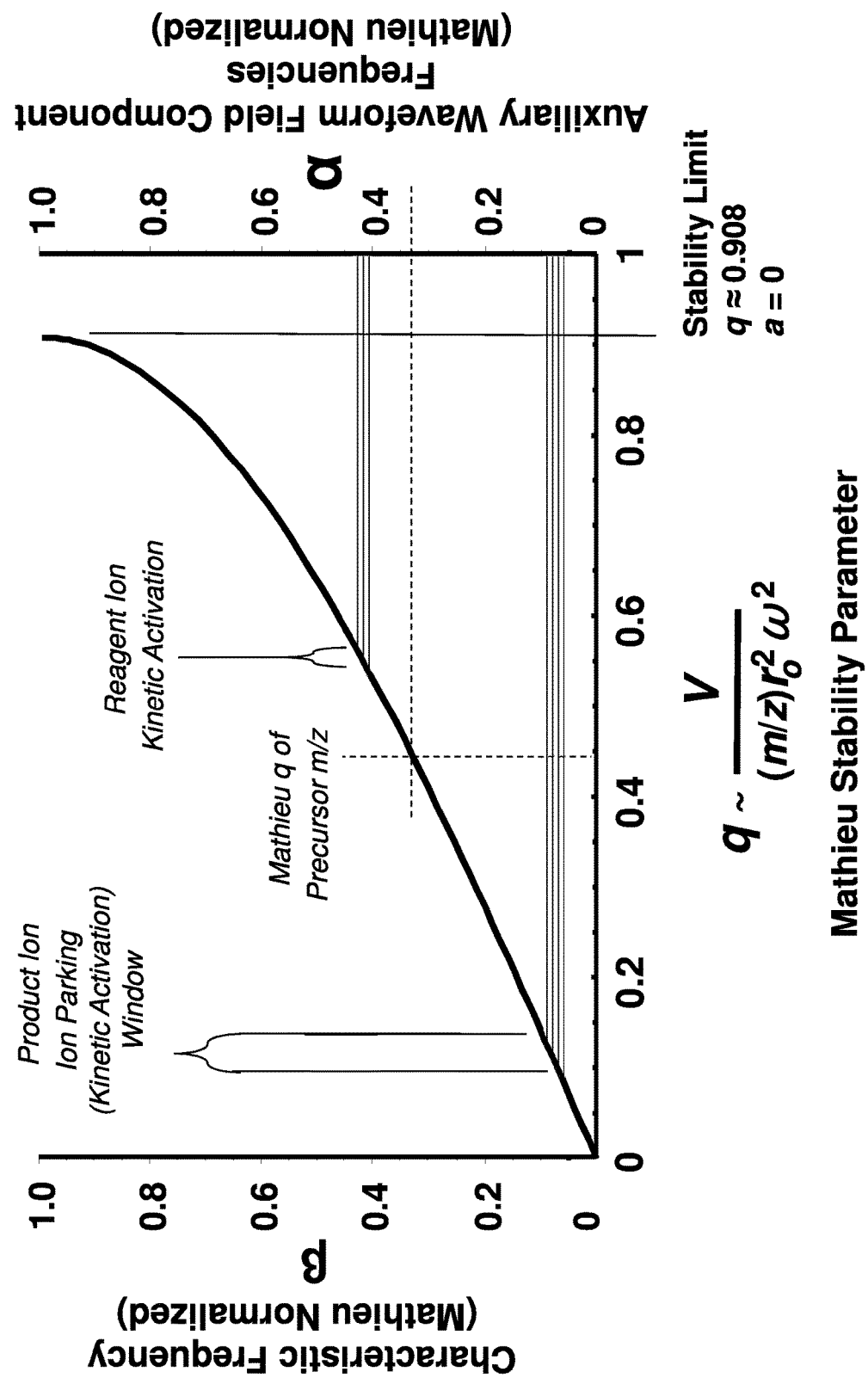
FIG. 10 Graph illustrating how the waveform component frequencies of the waveform depicted in FIG. 9 map on to a plot of Mathieu normalized ion characteristic frequency, $\beta$, versus Mathieu q parameter.
Figure 11:
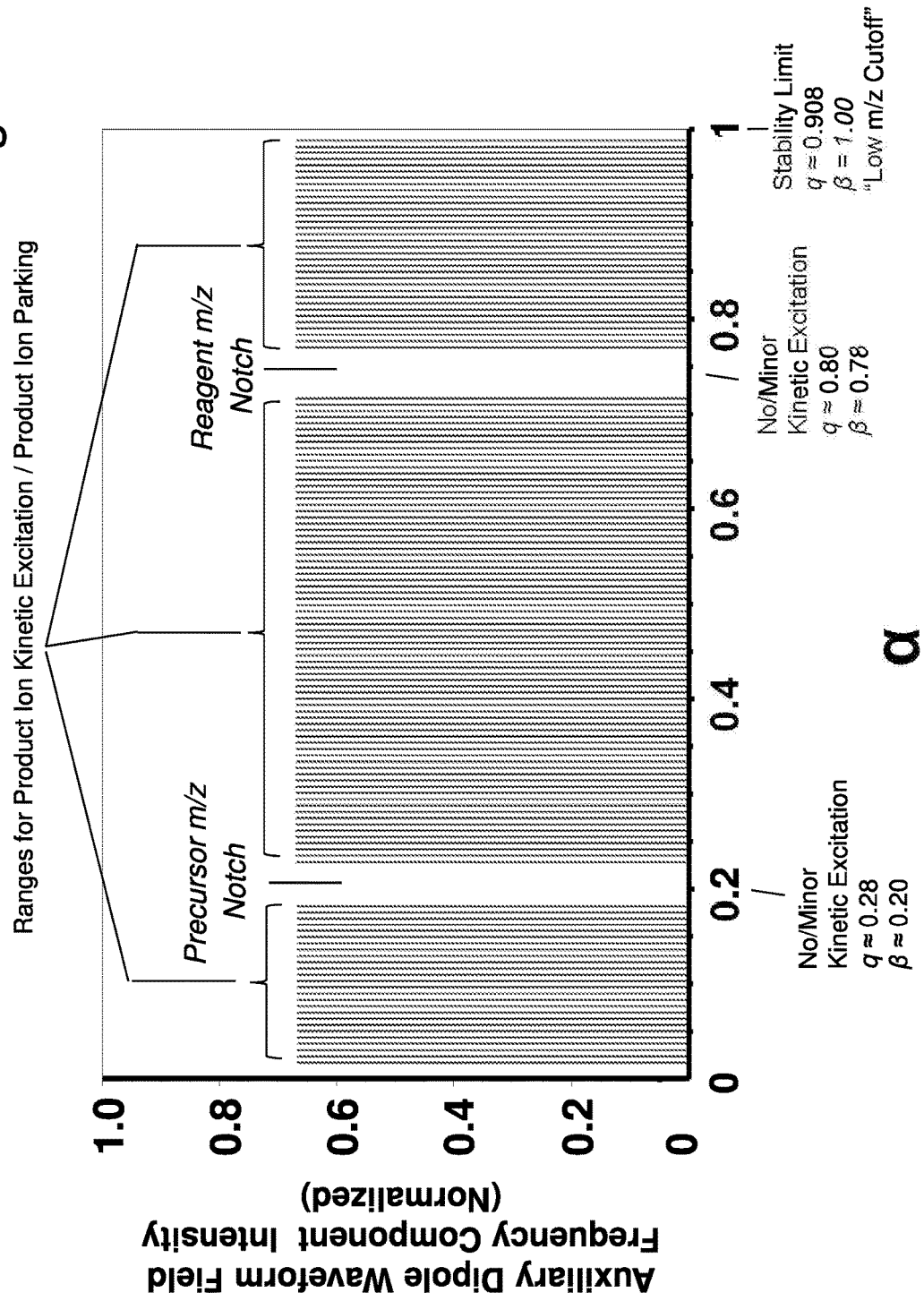
FIG. 11. Representation of the frequency composition of a broadband parking waveform constructed according to the prior art wherein the waveform frequency components (Mathieu normalized) have equal amplitude.
Figure 12:
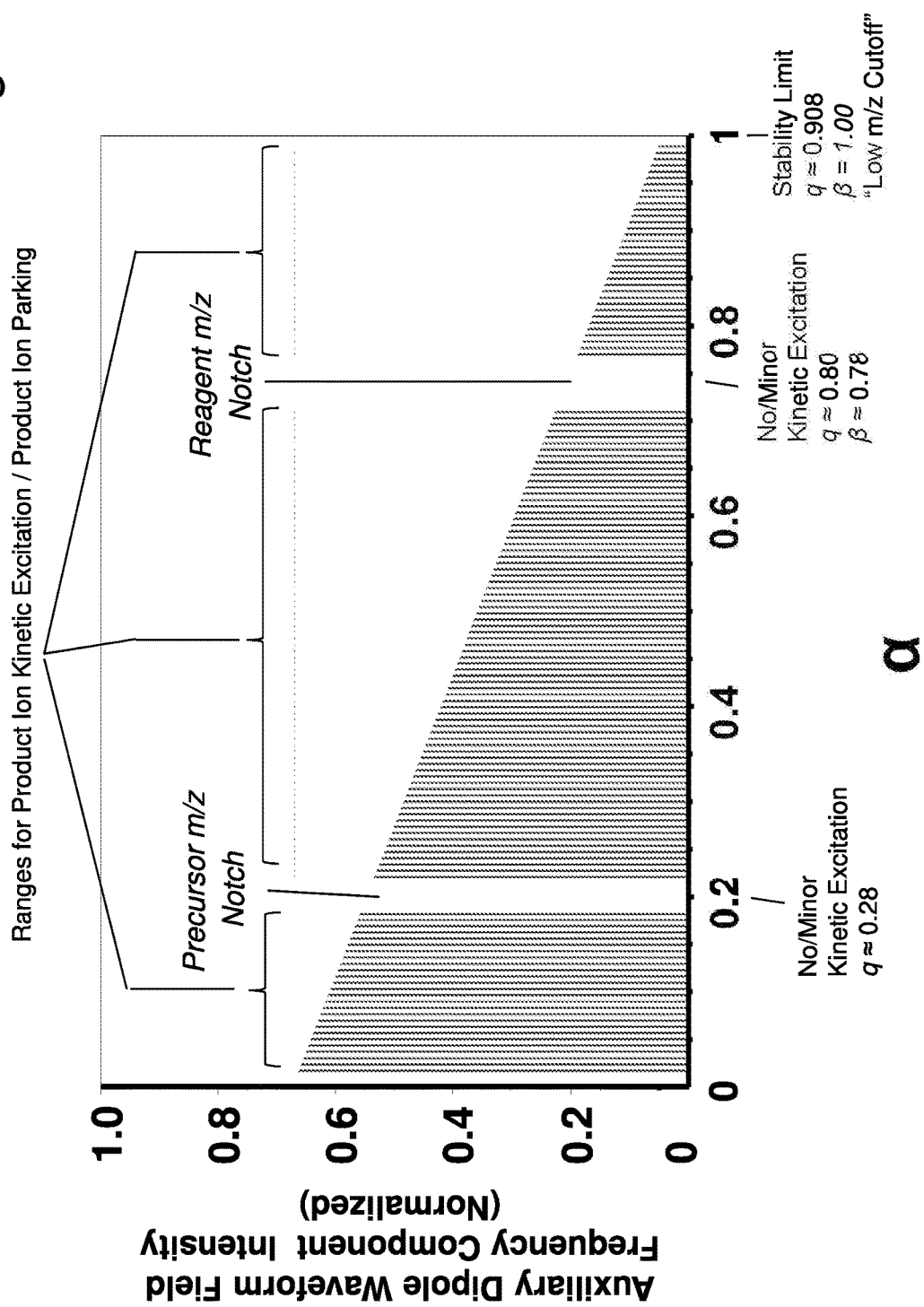
FIG. 12. Representation of the frequency composition (Mathieu normalized) of a broadband parking waveform according to the prior art wherein the waveform frequency components have amplitude that depends on frequency.
Figure 13:
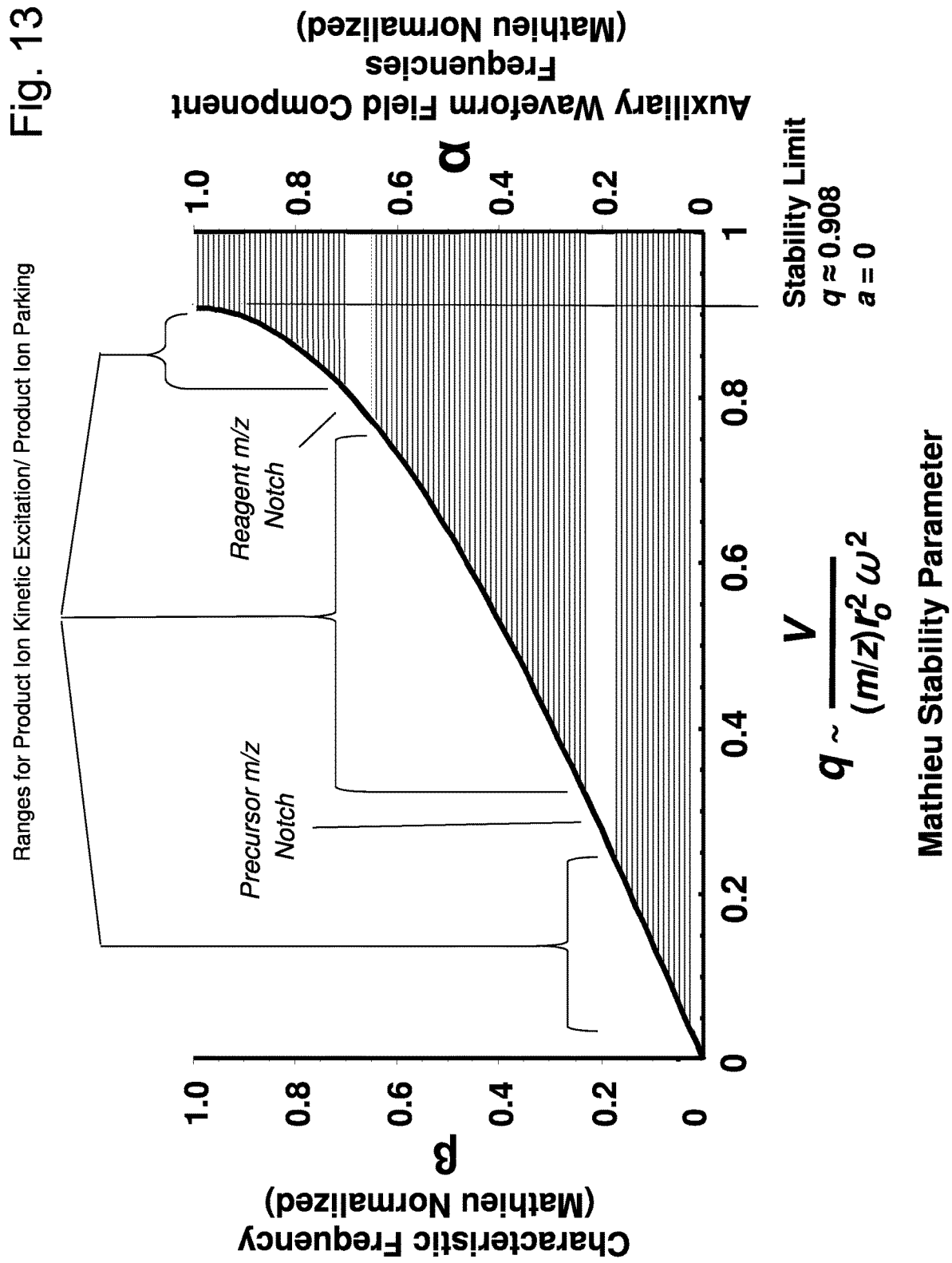
FIG. 13. For a broadband parking waveform constructed according to the prior art, an illustration of how its waveform frequency components (Mathieu normalized) map to ranges of ion characteristic frequency, $\beta$, and Mathieu parameter q in the quadrupole field which are subject to kinetic activation by the waveform field.

FIG. 10 shows how the waveform frequencies of FIG. 9 map on to a plot of Mathieu normalized ion characteristic frequency, $\beta$, versus Mathieu q parameter. This shows the how the reagent ions, which are held at q=0.55 may be kinetically activated by the band of waveform frequencies that correspond to ion characteristic frequencies that correspond to Mathieu q parameter values close to 0.55.

Figure 14:
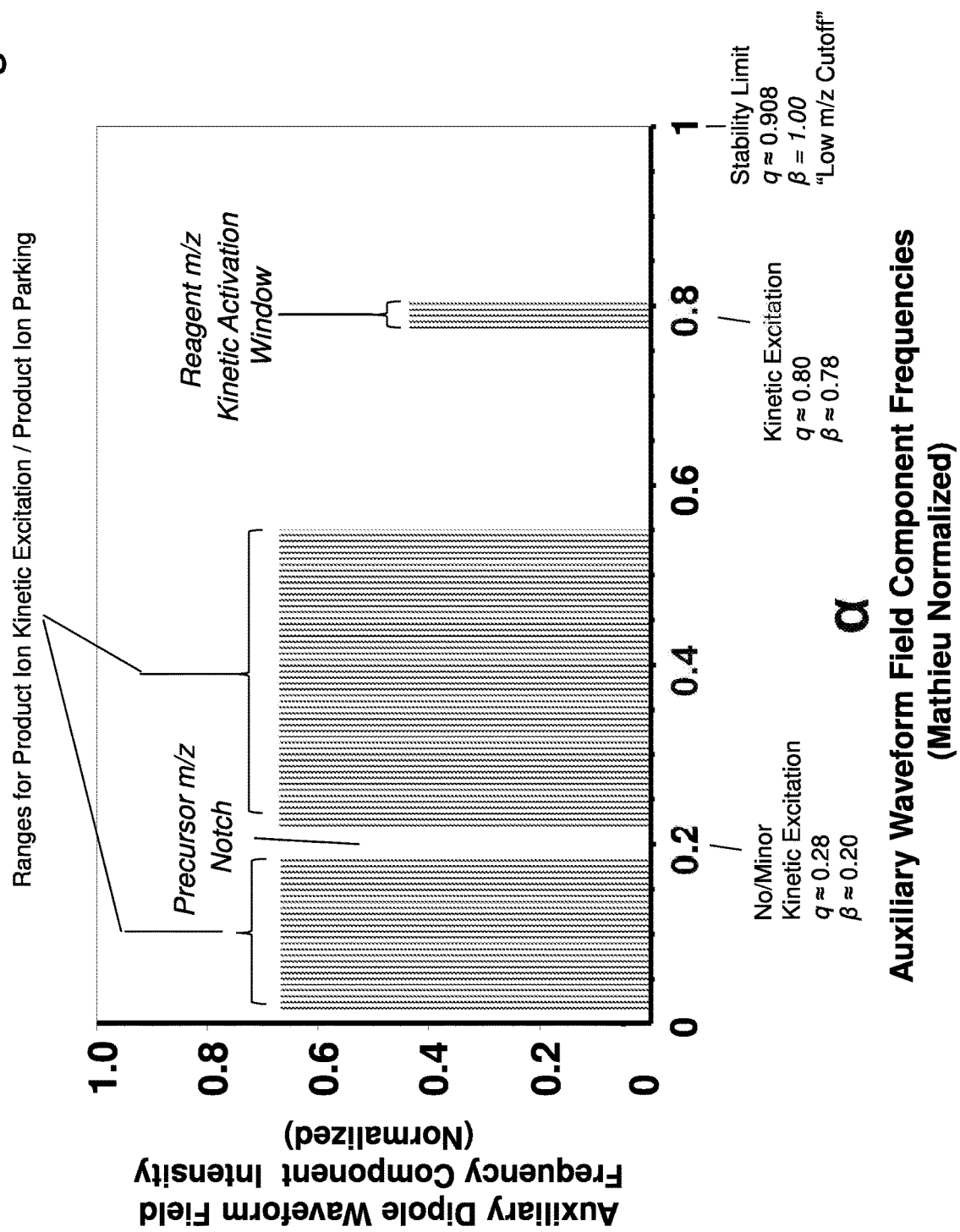
FIG. 14 Representation of the frequency composition of a broadband parking waveform constructed according to the disclosure wherein there are specific frequency components (Mathieu normalized) that serve to kinetically activate the reagent ions which have equal amplitude and there are waveform frequency components for kinetically activating analyte products ions which have equal amplitude. This would be representative of a suitable broadband parking waveform used for preserving large highly charged product ions from ETD of a highly charge protein precursor ion species.
Figure 16:
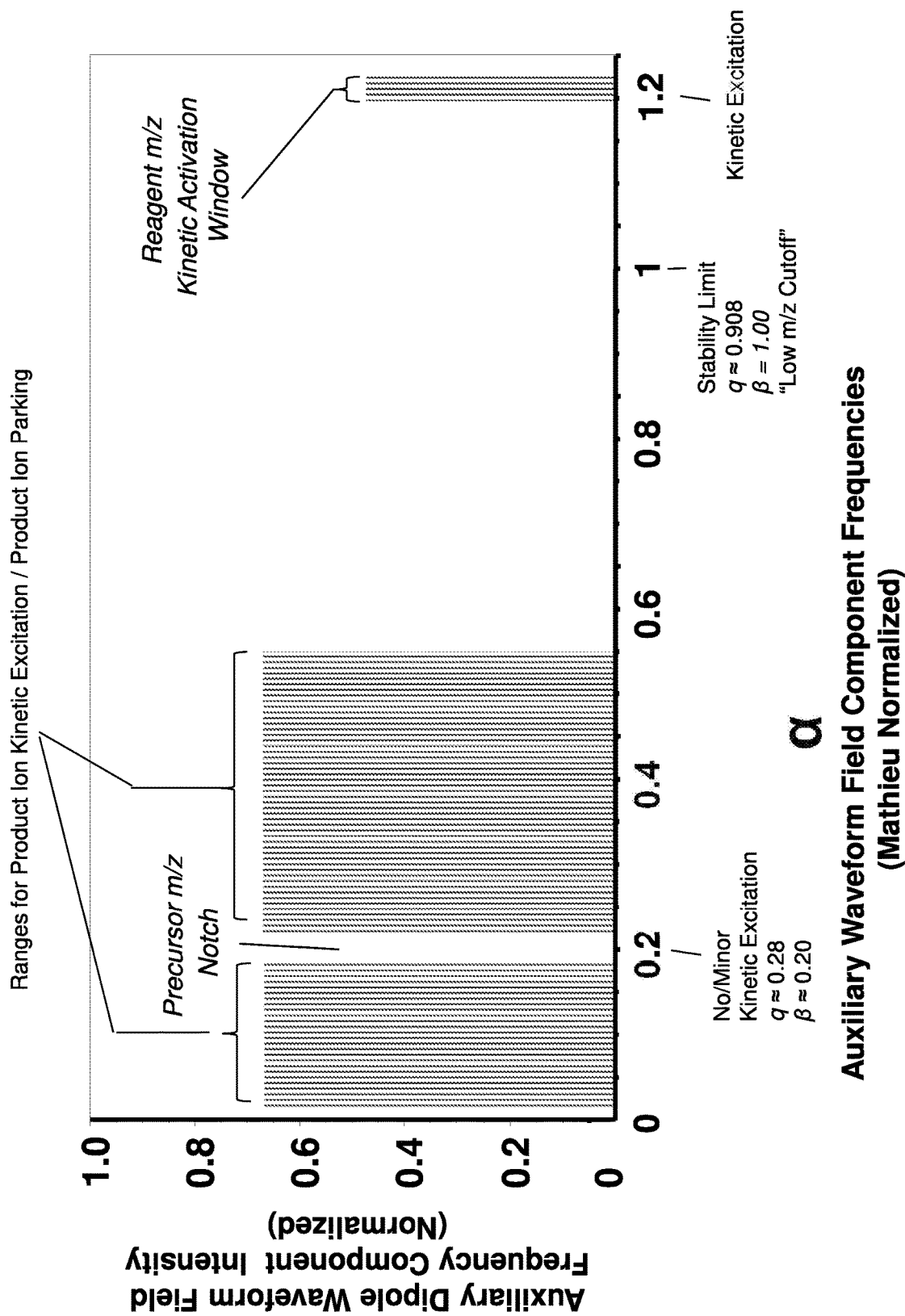
FIG. 16. Representation of the frequency composition of a broadband parking waveform constructed according to the invention wherein there are specific equal amplitude frequency components that serve to kinetically activate the reagent ions and the waveform frequency components for kinetically activating analyte product ions have equal amplitudes. The frequency components that serve to kinetically activate the reagent ions correspond to the second order, 2-$\beta$, ion resonant frequencies. This would be representative of a suitable broadband parking waveform used for preserving large highly charged product ions from ETD of a highly charge protein precursor ion species.
Figure 17:
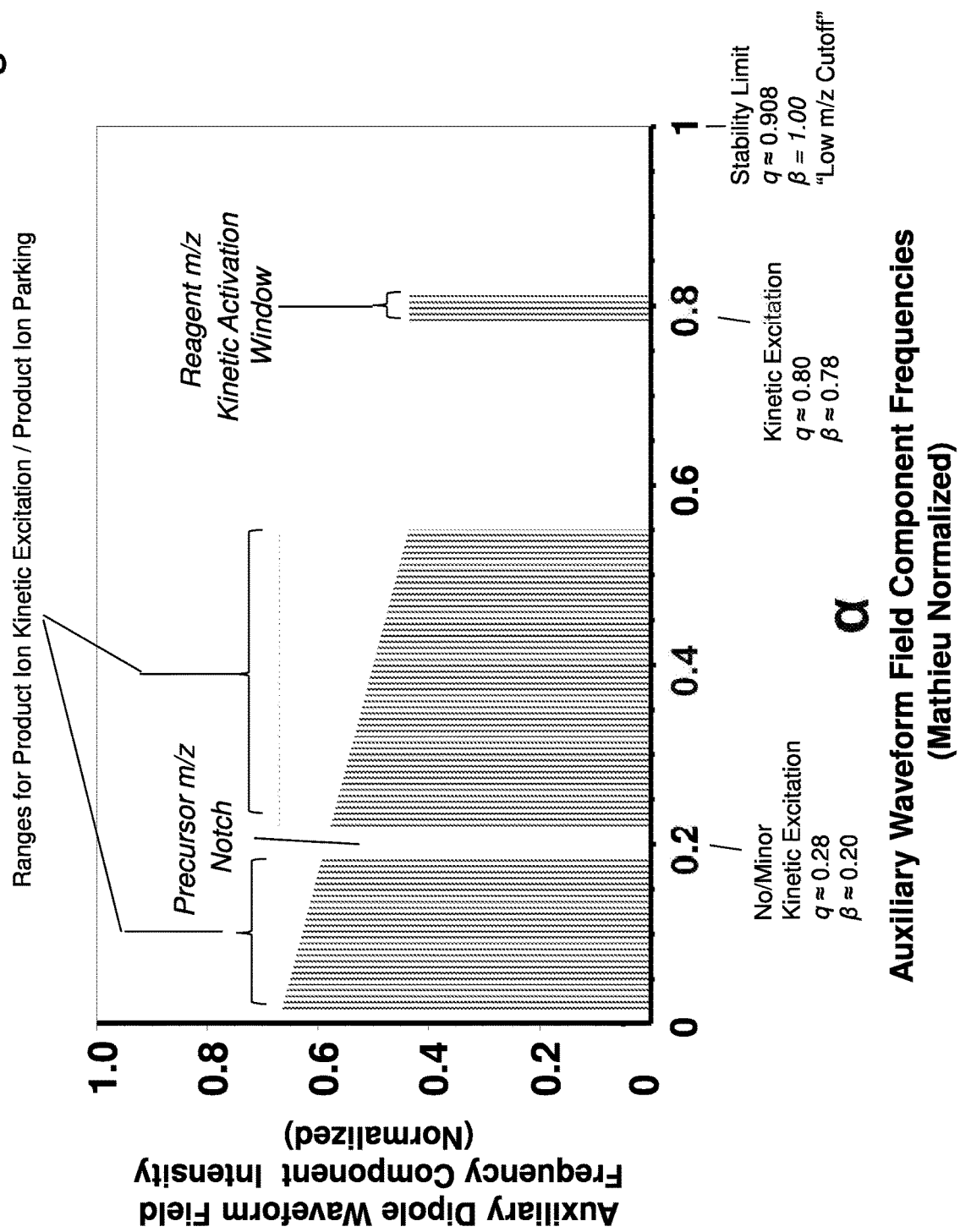
FIG. 17 Representation of the frequency composition of a broadband parking waveform constructed according to the invention wherein there are specific frequency components that serve to kinetically activate the reagent ions and the waveform frequency components for kinetically activating analyte product ions have amplitudes that depend on frequency. This would be representative of a suitable broadband parking waveform used for preserving large highly charged product ions from ETD of a highly charge protein precursor ion species.
Figure 18:
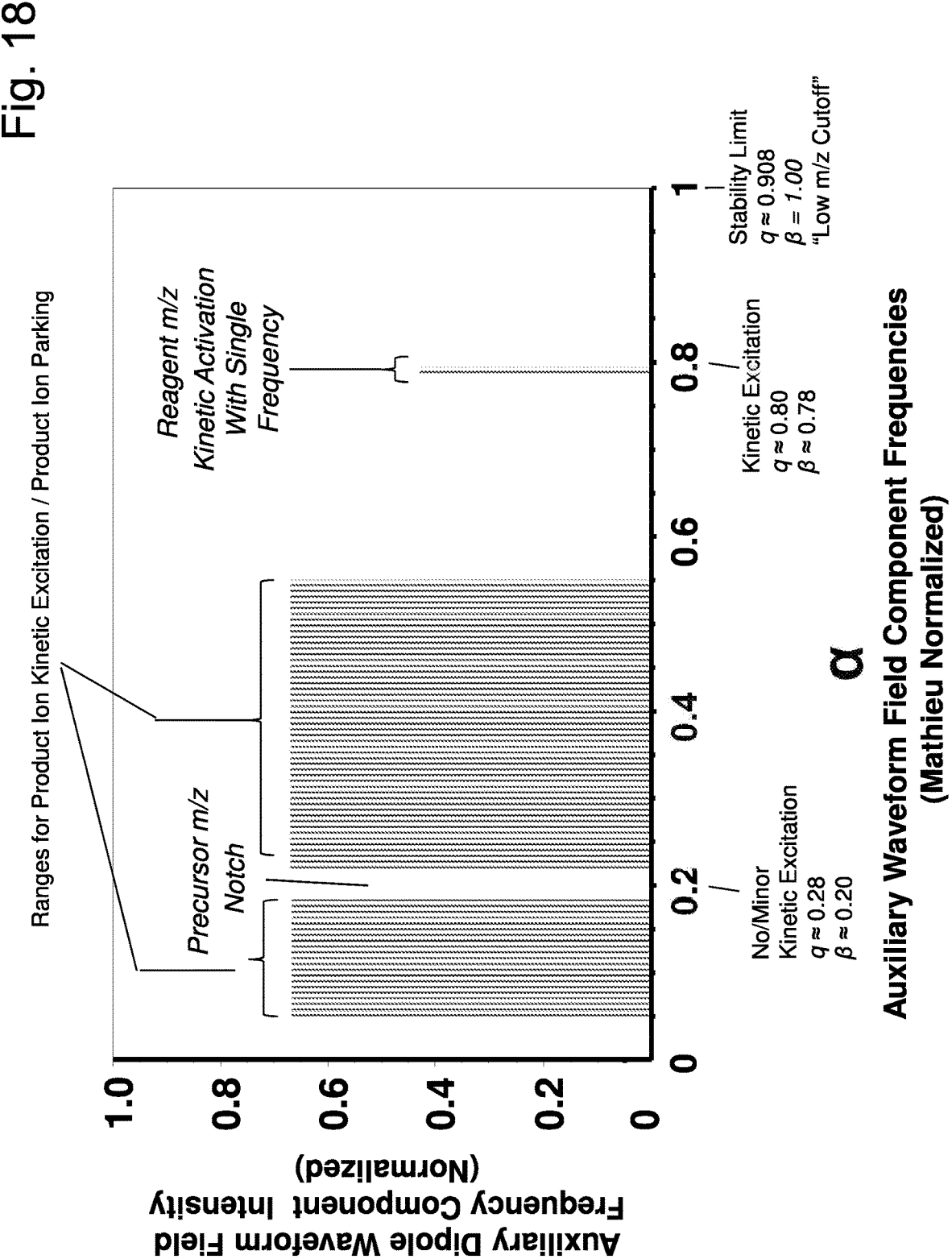
FIG. 18 Representation of the frequency composition of a broadband parking waveform constructed according to the invention wherein there is a specific (single) frequency component that serves to kinetically activate the reagent ions and the waveform frequency components for kinetically activating analyte products ions have equal amplitude. This would be representative of a suitable broadband parking waveform used for preserving large highly charged product ions from ETD of a highly charge protein precursor ion species.

Of course this is only one mode of operation for ion parking for ion-ion reactions in accordance with the invention. In other modes of the invention, the reagents ion may react with analyte ions by ETD, NETD, proton donation (Negative IIPT, NIIPT), ion attachment or other mechanisms. In a mode of the invention the dipole parking waveform component frequencies are comprised of a single frequency component for activation of the reagent ions (FIG. 18). In some modes of the invention the dipole parking waveform component frequencies are comprised of multiple frequency components for activation of the reagent ions (FIG. 14). In further modes of the invention, the dipole auxiliary field parking waveform component frequencies for are comprised of one or more frequency components that are or close to or equal to one of the higher order frequencies of ion motion in a RF quadrupole field. Such frequencies would include higher order Mathieu normalized frequencies of 2-$\beta$ and 2-$\beta$ where $\beta$ is the Mathieu normalized frequency of the reagent ions in the in a dimension that is driven by the auxiliary dipole waveform field (FIG. 16).

Figure 19A:
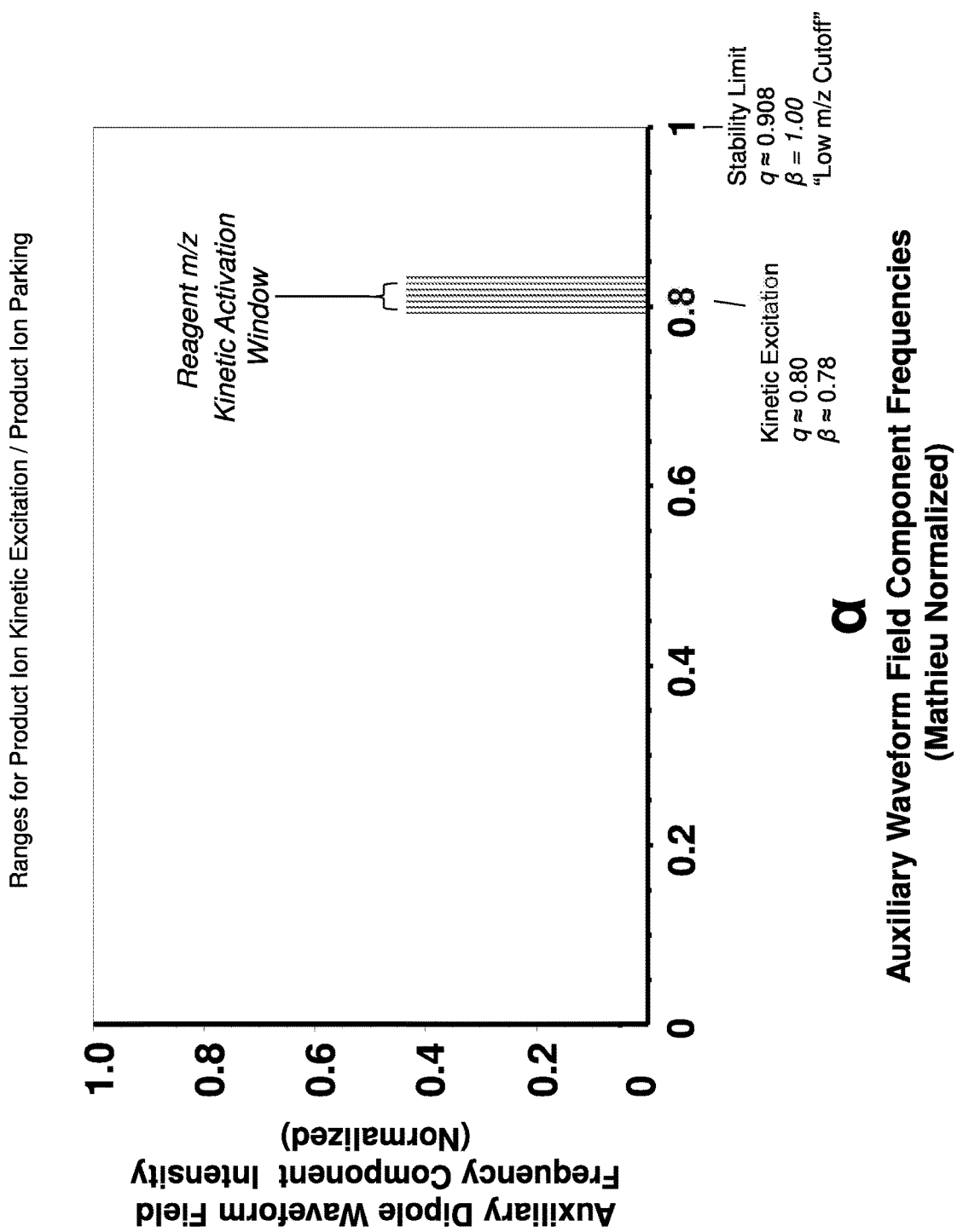
FIGS. 19A & 19B A representation of the frequency composition of a pair of broadband parking waveforms constructed according to the invention wherein in the first waveform (see FIG. 19A) there are specific frequency components that serve to kinetically activate the reagent ions and in the second waveform (See FIG. 19B) there are frequency components for kinetically activating analyte products ions which have equal amplitude. This would be representative of a suitable pair of waveforms which in combination provide broad band ion parking for preserving large highly charged product ions from ETD of a highly charged protein precursor ion species.
Figure 19B:
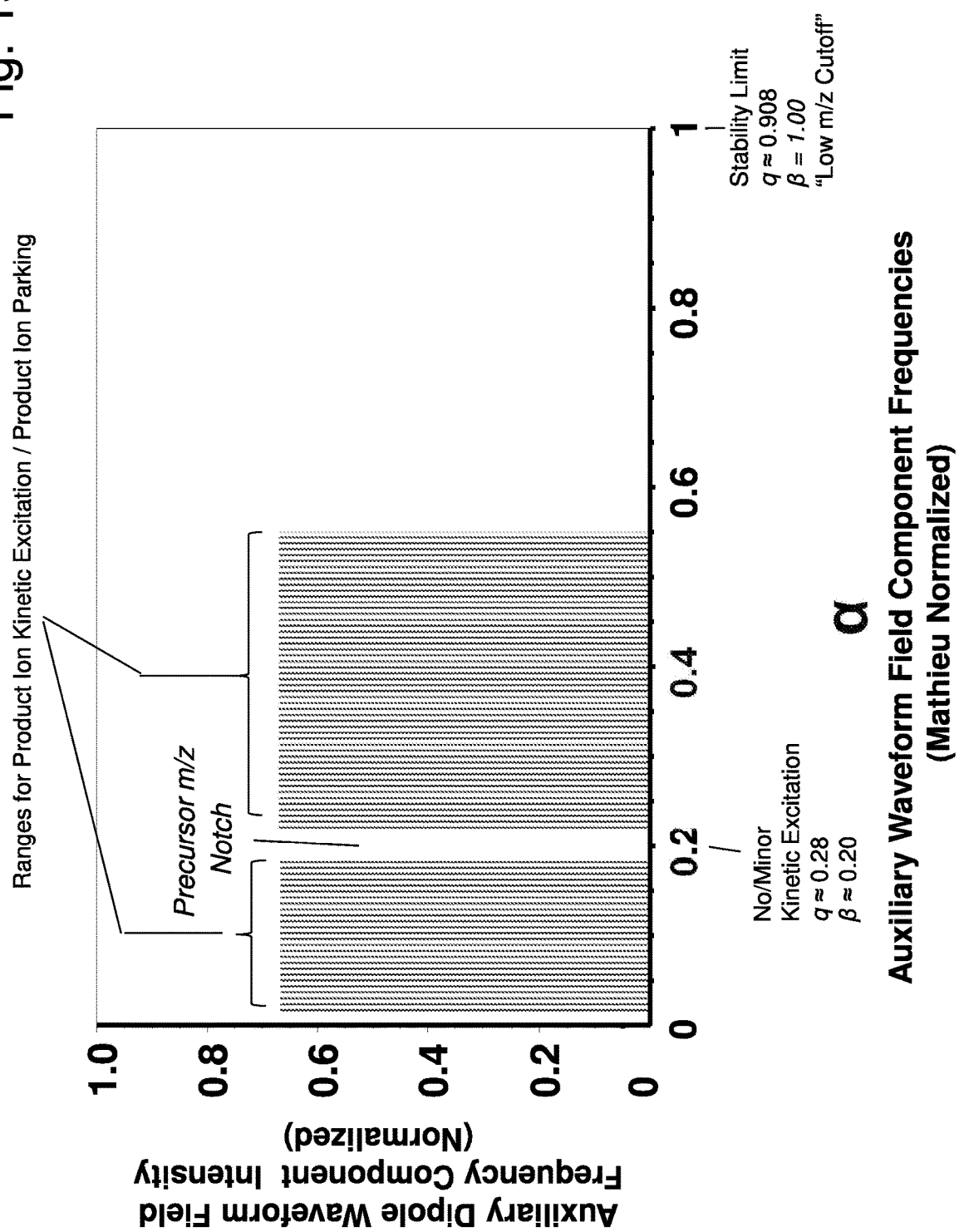

In another mode of the invention there are two applied auxiliary dipolar waveform fields applied during an ion-ion reaction. The first auxiliary dipole waveform field is oriented in a first dimension and is comprised of one or more frequencies that serve to kinetically excite range(s) of m/z of analyte induce ion parking of ions having frequencies within said range(s) (see FIG. 19B). The second auxiliary dipole field oriented a second dimension is comprised of a frequency or frequencies that serve to provide mild kinetic activation of reagent ions in a dimension orthogonal the dimension of kinetic excitation of the analyte product ions (FIG. 19B). FIG. 4 is a functional schematic showing for exemplary purposes how trapping RF voltages, the first waveform field voltages and the second waveform field voltages may be applied to achieve one such a superposition of fields.

A further mode of the invention is where during the ion-ion reaction, instead of kinetically exciting the reagent ions by the auxiliary dipole waveform field, an auxiliary AC quadrupole field comprised of at least one component frequency is superposed on the RF quadrupole trapping field, and the auxiliary dipole parking waveform field which is comprised of one or more frequency components for activating the analyte product ions in the m/z range, wherein the characteristic frequencies of the reagent ions are close to one of the parametric resonance frequencies associated the auxiliary quadrupole field. A preferred instances of this mode of this mode of the invention, the auxiliary quadrupole field has a single frequency so that, in Mathieu normalized terms, the parametric resonance frequencies for ions occur when ion characteristic frequencies $\beta$, correspond to $\beta=\alpha_2/2$ and $\beta=(2-\alpha_2)/2$ where $\alpha_2$ is the Mathieu normalized frequency of the auxiliary quadrupole field. For modes of the invention where said auxiliary quadrupole field a single component frequency, a particularly advantageous mode is where the frequency of the auxiliary quadrupole field is close to one half of the frequency that of the main quadrupole trapping field creating a pair of parametric resonances near $\beta=0.5$ (q≈0.64) if the main quadrupole trapping field is RF only and reagent ions are held in the trapping field such that their Mathieu q is in at least one dimension of the RF quadrupole trapping field.

A further mode of this invention is where instead of using auxiliary fields to excite the reagent ions during ion-ion reactions the reagent ions are held in a the field under conditions where they are excited by non-linear resonances associated with higher order field components of the generally predominantly quadrupolar main RF trapping field whilst product ions in the m/z range for ion parking are kinetically excited by the component frequencies of an auxiliary dipole parking waveform field. The common deviations from ideality in the electrode shape and positioning of many commercial quadrupole linear trap structures driven with RF only trapping potentials produce a non-linear resonances in the vicinity of $\beta=0.5$ (q≈0.64) so one version of this mode of the invention would be to hold reagent ions in a quadrupole linear ion trap at a Mathieu q close to this non-linear resonance.

In modes where the reagent ions are kinetically activated by being confined in the RF trapping field at conditions such that ions are near or on a non-linear resonance t is not generally possible to simply turn on or off the kinetic activation of the reagent ions by the application or removal off auxiliary potentials. Where non-linear resonances are utilized in this manner, the effect of reagent ion activation on reaction rate constants and kinetics of the ion-ion reactions can be determined by similar methods as described above except instead of comparing the case where the reagent ions activating frequency components of the auxiliary waveform field are either applied or not applied, the magnitude of the RF voltages used to establish the trapping fields which determine the ion characteristic frequencies of motion, are adjusted. Non-linear resonances are rather narrow in the range of m/z affected relative to the m/z at center of the resonance, so that relatively small changes in the applied RF trapping potentials (a few percent) will strongly affect the level of kinetic activation ions experience when confined in conditions near or on a non-linear resonance and thus reduce the measured ion-ion reaction rate constants. Changing the magnitude of the RF trapping potentials used during ion-ion reactions will also alter the reagent ion cloud radius and therefore alter concentration of reagent ions even without the influence of non-linear resonances. However the associated variation in reaction rate constants should have a considerably weaker dependence on the magnitude of the applied trapping voltage than the influence of a non-linear resonance. This will allow the contribution the kinetic excitation of reagent ions to change in ion-ion reaction rate constants to be assessed and quantified.

The above discussion general approaches to assessing and quantifying the magnitude the influence of various methods of reagent ion activation on the kinetics of ion-ion reactions in order to establish that this is feasible and reasonable. For analytically useful instruments, and, in particular, for commercially produced instruments to be used of analytical work which incorporate the inventive methods described herein, these types of measurements would be a natural part of the engineering process in developing these instruments. Indeed ion-ion rate constant measurements such as these are to be incorporated into the automated instrument calibration procedures that are used to permit automatic control and selection of advantageous (and in some cases optimal) setting of the parameters for the ion-ion reactions during analytical experiments. 2015 Rose et al provides an example of the sorts of calibrations. Along with reagent ion population (Target) and reaction time, the settings determining the degree of reagent activation advantageous or near optimal for performing particular parking experiments based on the m/z and charge state, z of ions would be determined by calibrations and be part of the instrument control software.

Experiments have been performed measuring the reaction rate constant k of a particular protein precursor charge state (rate constant of depletion) during IIPT reactions ions as a function of the amplitude of the of the parking waveform frequency band used to kinetically excite the reagent ions. Increasing the kinetic activation of the reagent ions provides a continuous reduction in k.

INCORPORATED BY REFERENCE

References

Books
2005 March and Todd
March, Raymond E., and John F. Todd. *Quadrupole ion trap mass spectrometry*. Vol. 165. John Wiley & Sons, 2005
1976 Dawson P H
Dawson P. H. Ed "Quadrupole mass spectrometry and its applications." *Elsevier, Amsterdam* (1976)
Journal Articles 1998 McLuckey and Stephenson
McLuckey, Scott A., and James L. Stephenson. "Ion/ion chemistry of high-mass multiply charged ions." *Mass spectrometry reviews* 17.6 (1998): 369-407.
2001 Lammert et al
Lammert, Stephen A., et al. "Design, optimization and initial performance of a toroidal rf ion trap mass spectrometer." *International Journal of Mass Spectrometry* 212.1 (2001): 25-40.
2002 Schwartz et al.
Schwartz, Jae C., Michael W. Senko, and John E. P. Syka. "A two-dimensional quadrupole ion trap mass spectrometer." *Journal of the American Society for Mass Spectrometry* 13.6 (2002): 659-669.
2002 Hager
Hager, James W. "A new linear ion trap mass spectrometer." *Rapid Communications in Mass Spectrometry* 16.6 (2002): 512-526.
2002 McLuckey et al.
McLuckey, Scott A., Gavin E. Reid, and J. Mitchell Wells. "Ion parking during ion/ion reactions in electrodynamic ion traps." *Analytical chemistry* 74.2 (2002): 336-346.
2002 Reid et al.
Reid, Gavin E., Hao Shang, Jason M. Hogan, Gil U. Lee, and Scott A. McLuckey. "Gas-phase concentration, purification, and identification of whole proteins from complex mixtures." *Journal of the American Chemical Society* 124.25 (2002): 7353-7362.
2003 Reid et al.
Reid, Gavin E., J. Mitchell Weds, Ethan R. Badman, and Scott A. McLuckey. "Performance of a quadrupole ion trap mass spectrometer adapted for ion/ion reaction studies." *International Journal of Mass Spectrometry* 222.1 (2003): 243-258.
2003 Hogan et al
Hogan, Jason M., Sharon J. Pitteri, and Scott A. McLuckey. "Phosphorylation site identification via ion trap tandem mass spectrometry of whole protein and peptide ions: bovine α-crystallin A chain." *Analytical chemistry* 75.23 (2003): 6509-6516.
2004 Syka et al.
Syka, John E P, Joshua J. Coon, Melanie J. Schroeder, Jeffrey Shabanowitz, and Donald F. Hunt"Peptide and protein sequence analysis by electron transfer dissociation mass spectrometry." *Proceedings of the National Academy of Sciences of the United States of America* 101.26 (2004) 9528-9533
2004 Coon et al.
Coon, Joshua J., John E P Syka, Jae C. Schwartz, Jeffrey Shabanowitz, and Donald F. Hunt. "Anion dependence in the partitioning between proton and electron transfer in ion/ion reactions." *International Journal of Mass Spectrometry* 236.1 (2004): 33-42.
2004 Wu et al.
Wu, Jin, James W. Hager, Yu Xia, Frank A. Londry, and Scott A. McLuckey. "Positive ion transmission mode ion/ion reactions in a hybrid linear ion trap." *Analytical chemistry* 76.17 (2004): 5006-5015.
2005 Coon et al.
Coon, Joshua J., et al. "Protein identification using sequential ion/ion reactions and tandem mass spectrometry." *Proceedings of the National Academy of Sciences of the United States of America* 102.27 (2005): 9463-9468.
2005 Coon et al.
Coon, Joshua J., et al. "Electron transfer dissociation of peptide anions." *Journal of the American Society for Mass Spectrometry* 16.6 (2005): 880-882.

2005 Chrisman et al.
Chrisman, Paul A., Sharon J. Pitteri, and Scott A. McLuckey. "Parallel ion parking: improving conversion of parents to first-generation products in electron transfer dissociation." *Analytical chemistry* 77.10 (2005): 3411-3414.
2005 Xia et al.
Xia, Yu, Jin Wu, Scott A. McLuckey, Frank A. Londry, and James W. Hager. "Mutual storage mode ion/ion reactions in a hybrid linear ion trap." *Journal of the American Society for Mass Spectrometry* 16.1 (2005): 71-81.
2006 Xia et al.
Xia, Yu, et al. "Implementation of ion/ion reactions in a quadrupole/time-of-flight tandem mass spectrometer." *Analytical chemistry* 78.12 (2006): 4146-4154.
2007 Liang et al.
Liang, Xiaorong, James W. Hager, and Scott A. McLuckey. "Transmission mode ion/ion electron-transfer dissociation in a linear ion trap." *Analytical chemistry* 79.9 (2007): 3363-3370.
2007 Liang and McLuckey
Liang, Xiaorong, and Scott A. McLuckey. "Transmission mode ion/ion proton transfer reactions in a linear ion trap." *Journal of the American Society for Mass Spectrometry* 18.5 (2007): 882-890.
2008 Kaplan et al.
Kaplan, Desmond A., et al. "Electron transfer dissociation in the hexapole collision cell of a hybrid quadrupole-hexapole Fourier transform ion cyclotron resonance mass spectrometer." *Rapid Communications in Mass Spectrometry* 22.3 (2008): 271-278.
2013 Rose et al.
Rose, Christopher M., Jason D. Russell, Aaron R. Ledvina, Graeme C. McAlister, Michael S. Westphall, Jens Griep-Raming, Jae C. Schwartz, Joshua J. Coon, and John E P Syka. "Multipurpose dissociation cell for enhanced ETD of intact protein species." *Journal of The American Society for Mass Spectrometry* 24.6 (2013): 816-827.
2013 Ledvina et al.
Ledvina, Aaron R., et al. "Activated ion ETD performed in a modified collision cell on a hybrid QLT-oribtrap mass spectrometer." *Journal of The American Society for Mass Spectrometry* 24.11 (2013): 1623-1633. 2013 Senko et al.
Senko, Michael W., et al. "Novel parallelized quadrupole/linear ion trap/Orbitrap tribrid mass spectrometer improving proteome coverage and peptide identification rates." *Analytical chemistry* 85.24 (2013): 11710-11714.
2014 Remes et al.
Remes, Philip M., et al. "Insight into the resonance ejection process during mass analysis through simulations for improved linear quadrupole ion trap mass spectrometer performance." *International Journal of Mass Spectrometry* 370 (2014): 44-57.
2015 Hendrickson et al.
Hendrickson, Christopher L., et al. "21 Tesla Fourier Transform Ion Cyclotron Resonance Mass Spectrometer: A National Resource for Ultrahigh Resolution Mass Analysis." *Journal of The American Society for Mass Spectrometry* 26.9 (2015): 1626-1632.
2015 Rose et al.
Rose, Christopher M., et al. "A calibration routine for efficient ETD in large-scale proteomics." *Journal of The American Society for Mass Spectrometry* 26.11 (2015): 1848-1857.
Patents U.S. Pat. No. 5,324,939
Louris, John N., and Dennis M. Taylor. "Method and apparatus for ejecting unwanted ions in an ion trap mass spectrometer." U.S. Pat. No. 5,324,939. 28 Jun. 1994.
U.S. Pat. No. 5,420,425
Bier, Mark E., and John E P Syka. "Ion trap mass spectrometer system and method." U.S. Pat. No. 5,420,425. 30 May 1995.
U.S. Pat. No. 6,570,151
Grosshans, Peter B., Chad M. Ostrander, and Craig A. Walla. "Methods and apparatus to control charge neutralization reactions in ion traps." U.S. Pat. No. 6,570,151, 27 May 2003.
U.S. Pat. No. 6,674,067
Grosshans, Peter B., Chad M. Ostrander, and Craig A. Walla. "Methods and apparatus to control charge neutralization reactions in ion traps." U.S. Pat. No. 6,674,067. 6 Jan. 2004.
U.S. Pat. No. 6,844,547
Syka, John E P. "Circuit for applying supplementary voltages to RF multipole devices." U.S. Pat. No. 6,844,547. 18 Jan. 2005
U.S. Pat. No. 7,026,613 Syka, John E P. "Confining positive and negative ions with fast oscillating electric potentials." U.S. Pat. No. 7,026,613. 11 Apr. 2006.
U.S. Pat. No. 7,064,317
McLuckey, Scott A., Gavin E. Reid, and James Mitchell Wells. "Method of selectively inhibiting reaction between ions." U.S. Pat. No. 7,064,317. 20 Jun. 2006.
U.S. Pat. No. 7,355,169
McLuckey, Scott A., Gavin E. Reid, and James Mitchell Wells. "Method of selectively inhibiting reaction between ions." U.S. Pat. No. 7,355,169. 8 Apr. 2008.
U.S. Pat. No. 7,456,397
Hartmer, Ralf, and Andreas Brekenfeld. "Ion fragmentation by electron transfer in ion traps." U.S. Pat. No. 7,456,397. 25 Nov. 2008.
U.S. Pat. No. 7,534,622
Hunt, Donald F., Joshua J. Coon, John. E. P. Syka, Jarrod A. Marto "Electron transfer dissociation for biopolymer sequence analysis." U.S. Pat. No. 7,534,622. 19 May 2009.
U.S. Pat. No. 7,692,142
Schwartz, Jae C., John E P Syka, and Scott T. Quarmby. "Differential-pressure dual ion trap mass analyzer and methods of use thereof." U.S. Pat. No. 7,692,142. 6 Apr. 2010.
U.S. Pat. No. 7,749,769
Hunt, Donald F., Joshua J. Coon, and John Edward Philip Syka. "Simultaneous sequence analysis of amino- and carboxy-termini." U.S. Pat. No. 7,749,769. 6 Jul. 2010.
U.S. Pat. No. 7,759,637
Thomson, Bruce. "Method for storing and reacting ions in a mass spectrometer." U.S. Pat. No. 7,759,637. 20 Jul. 2010.
U.S. Pat. No. 7,842,917
McLuckey, Scott A., Xiaorong Liang, and Yu Xia. "Method and apparatus for transmission mode ion/ion dissociation." U.S. Pat. No. 7,842,917. 30 Nov. 2010.
U.S. Pat. No. 8,314,384
Stoermer, Carsten, Karsten Michelmann, and Michael Schubert. "Mixed radio frequency multipole rod system as ion reactor." U.S. Pat. No. 8,314,384. 20 Nov. 2012.
U.S. Pat. No. 8,334,503
McLuckey, Scott A., Paul A. Chrisman, and Sharon J. Pitteri. "Parallel ion parking in ion traps." U.S. Pat. No. 8,334,503. 18 Dec. 2012.

U.S. Pat. No. 8,598,517

McLuckey, Scott A., Yu Xia, and Hongling Han. "Method and apparatus for activation of cation transmission mode ion/ion reactions." U.S. Pat. No. 8,598,517. 3 Dec. 2013.

U.S. Pat. No. 9,171,707

Syka, John E P, Philip D. Compton, and Donald F. Hunt. "Reagents for electron transfer dissociation in mass spectrometry analysis." U.S. Pat. No. 9,171,707. 27 Oct. 2015.

What is claimed is:

1. A method for m/z selectively arresting ion-ion reactions (ion parking) within the ion-ion reaction cell of a mass spectrometer system, said method comprising providing a reaction cell comprising reagent ions and a set of electrodes with one or more periodic RF confinement voltages applied to them wherein during ion-ion reactions in one or more dimensions of ion motion, ions have oscillatory motion frequencies that are primarily determined by their mass-to-charge ratios, applying one or more auxiliary voltage waveforms to one or more electrodes of the ion-ion reaction cell, during a period where ion-ion reactions are performed, such that a first set of frequency components of one or more of said auxiliary waveform voltages provides m/z selective kinetic excitation to the reagent ions, kinetically exciting analyte product ions produced from said ion-ion reactions within one or more selected m/z ranges, during said period where ion-ion reactions are performed, so as to partially or fully arrest the further reaction of said analyte product ions within said selected m/z ranges;

wherein the one or more auxiliary voltage waveforms include a plurality of frequency components selected to kinetically excite, via resonant or near-resonant excitation, analyte product ions within the one or more selected m/z ranges, and a notch corresponding to the m/z of the analyte precursor ion.

2. The method of claim 1 wherein the ion-ion reaction cell is one of the following types of devices a RF 2D quadrupole ion trap having one or more segments or sections a RF 3D quuadrupole ion traps a RF torriodal traps.

3. The method of claim 1 wherein the analyte product ions have a charge state of 9 or more charges.

* * * * *